US007728155B2

(12) United States Patent
Gross et al.

(10) Patent No.: US 7,728,155 B2
(45) Date of Patent: Jun. 1, 2010

(54) DIHYDROBENZOFURANYL ALKANAMINES AND METHODS FOR USING SAME AS CNS AGENTS

(75) Inventors: Jonathan Laird Gross, Cranbury, NJ (US); Gary Paul Stack, Ambler, PA (US); Hong Gao, Belle Mead, NJ (US)

(73) Assignee: Wyeth LLC, Madison, NJ (US)

( * ) Notice: Subject to any disclaimer, the term of this patent is extended or adjusted under 35 U.S.C. 154(b) by 1365 days.

(21) Appl. No.: 10/970,103

(22) Filed: Oct. 21, 2004

(65) Prior Publication Data

US 2005/0124692 A1 Jun. 9, 2005

Related U.S. Application Data

(60) Provisional application No. 60/514,266, filed on Oct. 24, 2003.

(51) Int. Cl.
C07D 307/92 (2006.01)
(52) U.S. Cl. ..................................... 549/458
(58) Field of Classification Search .................. 549/458
See application file for complete search history.

(56) References Cited

U.S. PATENT DOCUMENTS

| 3,513,239 | A |   | 5/1970 | Wiley ........................ 424/285 |
| 3,759,927 | A |   | 9/1973 | Huebner ...................... 543/20 |
| 5,008,286 | A | * | 4/1991 | Bair ........................... 514/468 |
| 5,767,132 | A |   | 6/1998 | Bottcher et al. ............. 514/337 |
| 6,255,324 | B1 |  | 7/2001 | Heindel et al. .............. 514/314 |
| 6,569,894 | B1 |  | 5/2003 | Takaki et al. ................ 514/469 |

FOREIGN PATENT DOCUMENTS

| DE | 2165276 | 7/1972 |
| EP | 254 642 A1 | 1/1988 |
| EP | 446 809 A1 | 9/1991 |
| EP | 640 602 A1 | 3/1995 |
| EP | 0 707 007 A1 | 4/1996 |
| EP | 846 683 A1 | 6/1998 |
| EP | 1 211 253 A1 | 6/2002 |
| EP | 1 348 708 A1 | 10/2003 |
| GB | 1 200 892 | 8/1970 |
| JP | 59186969 A2 | 10/1984 |
| JP | 05 339271 | 12/1993 |
| JP | 06316563 A2 | 11/1994 |
| JP | 2000007671 | 1/2000 |
| JP | 2000080091 A2 | 3/2000 |
| WO | WO 91/17144 A1 | 11/1991 |
| WO | WO 93/10089 A1 | 5/1993 |
| WO | WO 94/18193 A1 | 8/1994 |
| WO | WO 96/30367 A1 | 10/1996 |
| WO | WO 00/76990 A1 | 12/2000 |
| WO | WO 00/77001 A1 | 12/2000 |
| WO | WO 00/77010 A2 | 12/2000 |
| WO | WO 03/022813 A1 | 3/2003 |
| WO | WO 03/022814 A1 | 3/2003 |
| WO | WO 03/074051 A1 | 9/2003 |

OTHER PUBLICATIONS

Lucchetti et al, 123:256498 RN168823-00-5.*
Dauksas et al 81:23665a (1973) abstract best available.*
Patent Abstracts of Japan, vol. 018, No. 182 (C-1184), Mar. 29, 1994 & JP 05 339271 A (Kowa Co.), Dec. 21, 1993.
Morris, J. et al., "Synthesis and biological activity of a potent antiplatelet 7-aminofurochromone," Bioorg Med Chem Letts, 1994, 4(21):2621-2626.
McNeel, T. E. et al., "Synthetic Approaches to 4,8-Dimethyl-5-(N-pyridiniummethyl)-4'-5'-dihydropsoralens and 4,8-Dimethyl-5'-(N-aminomethyl)-4',5'-dihydropsoralens '1,2," Journal of Heterocyclic Chemistry, 2001, 38:909-916.
U.S. Appl. No. 10/970,714, filed Oct. 21, 2004, Gross et al.
U.S. Appl. No. 60/621,023, filed Oct. 21, 2004, Zhou et al.
U.S. Appl. No. 60/621,024, filed Oct. 21, 2004, Gontcharov et al.
Toyoshima, S. et al., "Studies on benzoheterocyclic derivatives. VII. Synthesis and pharmacological action of benzofuran derivatives," Yakugaku Zasshi. May 1968;88(5):503-12. Japanese. [English abstract included].
Shinozaki, K. et al., "Synthesis and thromboxane A2 antagonistic activity activity of indane derivatives," Bioorg Med Chem Lett. Feb. 8, 1999;9(3):401-6.
Allison, D. B. et al., "Antipsychotic-Induced Weight Gain: A Comprehensive Research Synthesis," Am. J. Psychiatry, 1999, 156:1686-1696.
Masand, P. S., "Weight gain associated with psychotropic drugs," Exp. Opin. Pharmacother., 2000, 1: 377-389.
Whitaker, R., "Atypical Antipsychotics: A Modest Advance in Treating Schizophrenia," Spectrum Life Sciences. Decision Resources, 2000, 2:1-9.
Schotte, A. et al., "Risperidone compared with new and reference antipsychotic drugs: in vitro and in vivo receptor binding," Psychopharmacology, 1996, 124: 57-73.

(Continued)

Primary Examiner—Janet L. Andres
Assistant Examiner—Raymond Covington
(74) Attorney, Agent, or Firm—Doina G. Ene

(57) ABSTRACT

Compounds of formula 1 or pharmaceutically acceptable salts thereof are provided:

Formula 1

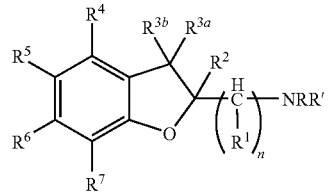

which are agonists and partial agonists of the 2c subtype of brain serotonin receptors. The compounds, and compositions containing the compounds, can be used to treat a variety of central nervous system disorders such as schizophrenia.

25 Claims, No Drawings

OTHER PUBLICATIONS

Cowen, P. J. et al., "Hypophagic, Endocrine and Subjective Responses to m- Chlorophenylpiperazine in Healthy Men and Women," Human Psychopharmacology, 1995, 10: 385-391.

Rosenzweig-Lipson, S. et al., "Antiobesity-like effects of the selective 5-HT2C Agonist Way," ASPET abstract, 2000.

Di Matteo, V. et al., "Selective blockade of serotonin$_{2C/2B}$ receptors enhances dopamine release in the rat nucleus accumbens," Nueropharmacology, 1998, 37: 265-272.

Fox, S. H. et al., "Behavioral Effects of 5-HT$_{2C}$ Receptor Antagonism in the Substantia Nigra Zona Reticulata of the 6-Hydroxydopamine-Lesioned Rat Model of Parkinson's Disease," Experimental Neurology, 1998, 151: 35-49.

Millan, M. J. et al., "Serotonin (5-HT)$_{2C}$ receptors tonically inhibit dopamine (DA) and noradrenaline (NA), but not 5-HT, release in the frontal cortex in vivo," Neuropharmacology, 1998, 37: 953-955.

Di Matteo, V. et al., "SB 242 084, a selective serotonin$_{2C}$ receptor antagonist, increases dopaminergic transmissions in the mesolimbic system," Nueropharmacology, 1999, 38: 1195-1205.

Di Giovanni, G. et al., "Preferential Modulation of Mesolimbic Vs. Nigrostriatal Dopaminergic Function by Serotonin$_{2C/2B}$ Receptor Agonists: A Combined In Vivo Electrophysiological and Microdialysis Study," Synapse, 2000, 35: 53-61.

Lloyd-Williams, P. et al., "Atropisomerism, biphenyls and the Suzuki coupling: peptide antibiotics," Chem. Soc. Rev., 2001, 30:145-157.

Wilen, S. H. et al., Tetrahedron, 1977, 33:2725-2736.

Wilen, S. H., Tables of Resolving Agents and Optical Resolutions, pp. 268-298, E.L. Eliel, Ed., Univ. of Notre Dame Press, Notre Dame, IN 1972.

Krogsgaard-Larson, et al., (ed.) Design and Application of Prodrugs, Textbook of Drug Design and Development, Ch. 5, 113-191 (1991).

Bundgaard, et al., Journal of Drug Delivery Reviews, 8:1-38 (1992).

Bundgaard, J. of Pharmaceutical Sciences, 77(4):285-298 (1988).

Higuchi and Stella (eds.) Prodrugs as Novel Drug Delivery Systems, American Chemical Society (1975) pp. 1-115 and 196-223.

Widder, et al. (ed.), Methods in Enzymology, vol. 4, Academic Press (1985) pp. 309-396.

Bundgaard (ed.), Design of Prodrugs, Elsevier (1985), Ch. 1 (pp. 1-92), Ch. 4 (pp. 157-176), Ch. 5 (pp. 177-198), and Ch. 6 (pp. 199-241).

Eliel, E.L., Stereochemistry of Organic Compounds, John Wiley & Sons, 1994, pp. 1142-1155.

Al-Bojuk, N. R. et al., "Synthesis and vasorelaxant potency of monagra. A chiral 5-(2-methyl-2,3-dihydro-7-bezofuryl)pyrazolopyrimidone analog of Viagra," Heterocycles, 2001, 55(9): 1789-1803.

Ferorelli, S. et al., "Lipase-mediated kinetic resolution of rigid clofibrate analogues with lipid-modifying activity," Tetrahedron: Asymmetry, 2001, 12(6): 853-862.

Ramadas, S. et al., "Enantioselective acylation of 2-hydroxymethyl-2,3-kihydrobenzofurans catalyzed by lipase from *Pseudomas cepacia* (Amano PS) and total stereoselective synthesis of (-)-(R)-MEM-protected arthrographol," Tetrahedron: Asymmetry, 2000, 11(16): 3375-3393.

Kakigami, T. et al., "Serotonin 5-HT4 receptor agonistic activity of the optical isomers of (±)-4-amino-N-[2-(1-azabicyclo[3.3.0]octan-5-yl)ethyl]-5-chloro-2,3-dihydro-2-methylbenzo[b]furan-7-carboxamide," Chemical & Pharmaceutical Bulletin, 1998, 46(6): 1039-1043.

Kuroita, T. et al., "Synthesis and structure-activity relationships of 2,3-dihydrobenzofuran-7-carboxamide derivatives as potent serotonin-3 (5-HT3) receptor antagonists," Chemical & Pharmaceutical Bulletin, 1994, 42(1): 95-100.

Takehara, S. et al., "New chiral dopants for FLC materials: optically active cyclic ethers," Ferroelectrics, 1993, 148(1-4): 195-202.

Ceccarelli, S. et.al., "Synthesis of novel 2-substituted-5-oxycoumarans via a direct route to 2,3-dihydro-5-hydroxy-2-benzofuranacetic acids," Journal of Heterocyclic Chemistry, May-Jun. 1993, 30(3): 679-90.

Ayer, W. et al., "Synthesis of (+/−) arthrographol," Canadian Journal of Chemistry, 1991, 69(12): 1909-1916.

Kemp, D. S. et al., "New templates for prior thiol capture from xanthene, dibenzo[c,h]xanthen-7-one and 2-methylenedihydrobenzofuran," Tetrahedron Letters, 1991, 32(26): 3009-3012.

Murakami, S. et al., "Antidopaminergic effects of the stereoisomers of N-[(1-alkyl-2-pyrrolidinyl)methyl]-5-sulfamoylbenzamides and -2,3-dihydro-benzofuran-7-carboxamides," Journal of Medicinal Chemistry, 1991, 34(1): 261-267.

Yodo, M. et al., "Optical resolution and chiral synthesis of methyl 6,7-dichloro-2,3-dihydrobenzo[b]furan-2-carboxylate," Chemical & Pharmaceutical Bulletin, 1988, 36(3): 902-913.

Chaudhuri, N. K. et al., "The absolute configuration of SU 23397: a novel neuroleptic agent," Experientia, 1977, 33(5): 575-577.

Grundon, M. et al., "Aysmmetric induction in the cyclization of 0-allylphenol with chiral mercury(II) carboxylates," Journal of the Chemical Society, Chemical Communications, 1973, 16: 573-574.

Jacques, et al., Enantiomers, Racemates and Resolutions Wiley Interscience, New York, 1981.

Eliel, E. L., Stereochemistry of Carbon Compounds McGraw-Hill, NY, 1962.

Remington's Pharmaceutical Sciences, 17$^{th}$ edition, ed. Alfonoso R. Gennaro, Mack Publishing Company, Easton, PA (1985).

* cited by examiner

DIHYDROBENZOFURANYL ALKANAMINES AND METHODS FOR USING SAME AS CNS AGENTS

CROSS REFERENCE TO RELATED APPLICATIONS

The present invention claims priority benefit of U.S. Provisional Application Ser. No. 60/514,266, filed Oct. 24, 2003, which is incorporated herein by reference in its entirety for all purposes.

FIELD OF THE INVENTION

The present invention relates to novel 1-(2,3,-dihydro-1-benzofuran-2-yl)alkanamine derivatives that act as agonists and partial agonists of the 5-HT$_{2C}$ receptor, processes for their preparation, and their use in medicine.

BACKGROUND OF THE INVENTION

Schizophrenia affects approximately 5 million people. The most prevalent treatments for schizophrenia are currently the 'atypical' antipsychotics, which combine dopamine (D$_2$) and serotonin (5-HT$_{2A}$) receptor antagonism. Despite the reported improvements in efficacy and side-effect liability of atypical antipsychotics relative to typical antipsychotics, these compounds do not appear to adequately treat all the symptoms of schizophrenia and are accompanied by problematic side effects, such as weight gain (Allison, D. B., et. al., Am. J. Psychiatry, 156: 1686-1696, 1999; Masand, P. S., Exp. Opin. Pharmacother. I: 377-389, 2000; Whitaker, R., Spectrum Life Sciences. Decision Resources. 2:1-9, 2000).

Atypical antipsychotics also bind with high affinity to 5-HT$_{2C}$ receptors and function as 5-HT$_{2C}$ receptor antagonists or inverse agonists. Weight gain is a problematic side effect associated with atypical antipsychotics such as clozapine and olanzapine, and it has been suggested that 5-HT$_{2C}$ antagonism is responsible for the increased weight gain. Conversely, stimulation of the 5-HT$_{2C}$ receptor is known to result in decreased food intake and body weight (Walsh et. al., Psychopharmacology 124: 57-73, 1996; Cowen, P. J., et. al., Human Psychopharmacology 10: 385-391, 1995; Rosenzweig-Lipson, S., et. al., ASPET abstract, 2000).

Several lines of evidence support a role for 5-HT$_{2C}$ receptor agonism or partial agonism as a treatment for schizophrenia. Studies suggest that 5-HT$_{2C}$ antagonists increase synaptic levels of dopamine and may be effective in animal models of Parkinson's disease (Di Matteo, V., et. al., Neuropharmacology 37: 265-272, 1998; Fox, S. H., et. al., Experimental Neurology 151: 35-49, 1998). Since the positive symptoms of schizophrenia are associated with increased levels of dopamine, compounds with actions opposite to those of 5-HT$_{2C}$ antagonists, such as 5-HT$_{2C}$ agonists and partial agonists, should reduce levels of synaptic dopamine. Recent studies have demonstrated that 5-HT$_{2C}$ agonists decrease levels of dopamine in the prefrontal cortex and nucleus accumbens (Millan, M. J., et. al., Neuropharmacology 37: 953-955, 1998; Di Matteo, V., et. al., Neuropharmacology 38: 1195-1205, 1999; Di Giovanni, G., et. al., Synapse 35: 53-61, 2000), brain regions that are thought to mediate critical antipsychotic effects of drugs like clozapine. However, 5-HT$_{2C}$ agonists do not decrease dopamine levels in the striatum, the brain region most closely associated with extrapyramidal side effects. In addition, a recent study demonstrates that 5-HT$_{2C}$ agonists decrease firing in the ventral tegmental area (VTA), but not in the substantia nigra. The differential effects of 5-HT$_{2C}$ agonists in the mesolimbic pathway relative to the nigrostriatal pathway suggest that 5-HT$_{2C}$ agonists have limbic selectivity, and will be less likely to produce extrapyramidal side effects associated with typical antipsychotics.

SUMMARY OF THE INVENTION

The present invention relates to certain dihydrobenzofuranyl alkanamine derivatives and to their use in medicine. In one aspect, the invention relates to novel 1-(2,3-dihydro-1-benzofuran-2-yl)alkanamine derivatives that act as agonists or partial agonists of the 5-HT$_{2C}$ receptor. The compounds can be used, for example, to treat schizophrenia and the concomitant mood disorders and cognitive impairments of schizophrenia. Compounds of the present invention are preferably less likely to produce the body weight increases associated with current atypical antipsychotics. The compounds of the present invention can also be used for the treatment of obesity and its comorbidities.

In certain embodiments, the invention relates to compounds of formula 1:

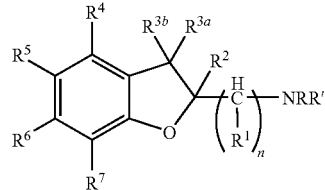

Formula 1 or pharmaceutically acceptable salts thereof;

wherein

R and R' are, independently, hydrogen, alkyl of 1 to 6 carbon atoms, cycloalkyl of 3 to 6 carbon atoms, or alkylcycloalkyl of 4 to 12 carbon atoms having 3 to 6 carbons in the cycloalkyl ring;

alternatively R and R' can be taken together with the nitrogen to which they are attached to form a ring containing 2-5 carbon atoms, wherein one of the ring carbon atoms is optionally replaced by nitrogen, sulfur or oxygen.

R$^1$ and R$^2$ are each, independently, hydrogen, alkyl of 1 to 6 carbon atoms, cycloalkyl of 3 to 6 carbon atoms, or perfluoroalkyl of 1 to 6 carbon atoms;

R$^{3a}$ and R$^{3b}$ are, independently, hydrogen, halogen, hydroxyl, alkyl of 1 to 6 carbon atoms, perfluoroalkyl of 1 to 6 carbon atoms, alkoxy of 1 to 6 carbon atoms, or perfluoroalkoxy of 1 to 6 carbon atoms;

two adjacent substituents selected from R$^4$ and R$^5$, or R$^5$ and R$^6$, or R$^6$ and R$^7$, together with the carbon atoms to which they are attached, form a cyclic moiety selected from a monocyclic cycloalkyl of 3 to 8 carbon atoms, a bridged cycloalkyl of 5 to 10 carbon atoms, a 3 to 8 membered heterocycloalkyl having 1 to 3 heteroatoms each independently selected from nitrogen, oxygen, or sulfur, aryl of 5 to 10 carbon atoms, or a 5 to 10 membered heteroaryl having 1 to 3 heteroatoms each independently selected from nitrogen, oxygen, or sulfur, wherein the monocyclic cycloalkyl or the heterocycloalkyl cyclic moiety may be optionally substituted at a single carbon atom with a cycloalkyl of 3 to 5 carbon atoms or a 3 to 5 membered heterocycloalkyl containing 1 or 2 heteroatoms each independently selected from nitrogen, oxygen, or sulfur, to form a spirocyclic group;

the remaining $R^4$ to $R^7$ substituents are, independently, hydrogen, halogen, cyano, hydroxyl, carboxyl, alkyl of 1 to 8 carbon atoms, perfluoroalkyl of 1 to 6 carbon atoms, alkoxy of 1 to 6 carbon atoms, perfluoroalkoxy of 1 to 6 carbon atoms, aryl of 5 to 10 carbon atoms, aryloxy of 5 to 10 carbon atoms, 5 to 10 membered heteroaryl having 1 to 3 heteroatoms each independently selected from nitrogen, oxygen or sulfur, alkenyl of 2 to 8 carbon atoms, alkanoyl of 2 to 6 carbon atoms, alkanoyloxy of 2 to 6 carbon atoms, carboalkoxy of 2 to 6 carbon atoms, carboxamido, alkanamido of 2 to 6 carbon atoms, alkanesulfonamido of 1 to 6 carbon atoms, amino, monoalkylamino of 1 to 6 carbon atoms, dialkylamino of 1 to 6 carbon atoms per alkyl moiety, cycloalkyl of 3 to 8 carbon atoms, or 3 to 8 membered heterocycloalkyl having 1 to 3 heteroatoms each independently selected from nitrogen, oxygen or sulfur; and n is 1, 2 or 3;

wherein any cycloalkyl or heterocycloalkyl group is saturated or partially saturated, and any aryl, heteroaryl, cycloalkyl, or heterocycloalkyl group may optionally be substituted with 1 to 5 substituents independently selected from halogen, hydroxyl, alkyl of 1 to 6 carbon atoms, perfluoroalkyl of 1 to 6 carbon atoms, alkoxy of 1 to 6 carbon atoms, or perfluoroalkoxy of 1 to 6 carbon atoms.

In certain other embodiments, the invention relates to methods for treating a patient suffering from a condition selected from schizophrenia, schizophreniform disorder, schizoaffective disorder, delusional disorder, substance-induced psychotic disorder, L-DOPA-induced psychosis, psychosis associated with Alzheimer's dementia, psychosis associated with Parkinson's disease, psychosis associated with Lewy body disease, dementia, memory deficit, intellectual deficit associated with Alzheimer's disease, bipolar disorders, depressive disorders, mood episodes, anxiety disorders, adjustment disorders, eating disorders, epilepsy, sleep disorders, migraines, sexual dysfunction, substance abuse, addiction to alcohol and various other drugs, including cocaine and nicotine, gastrointestinal disorders, obesity, or a central nervous system deficiency associated with trauma, stroke, or spinal cord injury that includes administering to the patient a therapeutically effective amount of a compound of formula 1, or a pharmaceutically acceptable salt thereof.

In still other embodiments, the invention relates to compositions comprising a compound of formula 1 or a pharmaceutically acceptable salt thereof, and one or more pharmaceutically acceptable carriers, excipients, or diluents.

DETAILED DESCRIPTION OF ILLUSTRATIVE EMBODIMENTS

The present invention relates to novel 1-(2,3,-dihydro-1-benzofuran-2-yl)alkanamine derivatives that are agonists or partial agonists of the 2c subtype of brain serotonin receptors.

The term "alkyl," as used herein, refers to an aliphatic hydrocarbon chain having up to 8 carbon atoms, preferably 1 to 6 carbon atoms, and more preferably 1 to 4 carbon atoms. The term "alkyl" includes, but is not limited to, straight and branched chains such as methyl, ethyl, n-propyl, isopropyl, n-butyl, isobutyl, sec-butyl, t-butyl, n-pentyl, isopentyl, neopentyl, n-hexyl, and isohexyl. In some embodiments, the alkyl group is preferably branched having 3 to 8 carbon atoms. The term "lower alkyl" refers to an alkyl group having 1 to 3 carbon atoms.

The term "alkenyl," as used herein refers to an aliphatic straight or branched hydrocarbon chain having 2 to 8 carbon atoms that may contain 1 to 3 double bonds. Examples of alkenyl groups include vinyl, prop-1-enyl, allyl, methallyl, but-1-enyl, but-2-enyl, but-3-enyl, or 3,3-dimethylbut-1-enyl. In some embodiments, the alkenyl is preferably a branched alkenyl of 3 to 8 carbon atoms.

The term "cycloalkyl," as used herein, refers to a saturated or partially saturated, hydrocarbon ring containing 3 to 10 carbon atoms, preferably 3 to 8 carbon atoms, and more preferably 5 to 7 carbon atoms. Unless explicitly stated otherwise herein, cycloalkyl groups may be monocyclic or bicyclic. Preferably, the cycloalkyl is monocyclic. Bicyclic cycloalkyl groups are preferably bridged containing 5 to 10 carbon atoms. "Bridged" refers to a cycloalkyl group that contains at least one carbon-carbon bond between two non-adjacent carbon atoms of the cycloalkyl ring. Preferably, the cycloalkyl group is saturated. The cycloalkyl group may be unsubstituted or substituted as described hereinafter.

The term "alkylcycloalkyl," as used herein, refers to the group —R-cycloalkyl, where cycloalkyl is as defined above and R is an alkyl moiety having 1 to 6, preferably 1 to 4, and more preferably 1 to 3 carbon atoms.

The term "heterocycloalkyl," as used herein, refers to a 3 to 8 membered, and more preferably 5 to 7 membered cycloalkyl group in which one to three carbon atoms of the cycloalkyl group are replaced with a heteroatom independently selected from oxygen, nitrogen, or sulfur. The heterocycloalkyl group may be saturated or partially saturated, and unless stated otherwise may be monocyclic or bicyclic (such as bridged). Preferably, the heterocycloalkyl is monocyclic. The heterocycloalkyl group may be unsubstituted or substituted as described hereinafter.

"Partially saturated," as used herein refers to a nonaromatic cycloalkyl or heterocycloalkyl group containing at least one double bond and preferably one or two double bonds.

The term "spirocyclic," as used herein, refers to two optionally substituted cycloalkyl groups, two optionally substituted heterocycloalkyl groups, or one optionally substituted cycloalkyl group and one optionally substituted heterocycloalkyl group that are joined by a single sp3 carbon atom that is the only common member of the two joined rings.

The term "aryl," as used herein refers to a 5 to 10 membered carbocyclic aromatic ring. Unless stated otherwise, the aryl may be monocyclic or bicyclic, and may be substituted or unsubstituted. Monocyclic aryl groups preferably have 5, 6, or 7 members and bicyclic aryl groups preferably have 8, 9 or 10 members. Exemplary aryl groups include phenyl and naphthyl.

The term "aryloxy," as used herein, refers to the group Ar—O—, where Ar is an aryl group of 5 to 10 carbon atoms as previously described.

The term "heteroaryl," as used herein, unless stated otherwise, refers to a 5 to 10 membered monocyclic or bicyclic carbon containing aromatic ring having 1 to 3 of its ring members independently selected from nitrogen, sulfur or oxygen. Monocyclic rings preferably have 5 to 6 members and bicyclic rings preferably have 8 to 10 membered ring structures. The heteroaryl group may be unsubstituted or substituted as described hereinafter. Examples of heteroaryls include, but are not limited to, thienyl, furyl, pyrrolyl, imidazolyl, pyrazolyl, oxazolyl, isoxazolyl, thiazolyl, isothiazolyl, pyridyl, pyrazinyl, pyrimidinyl, pyridazinyl, indolyl, indazolyl, benzofuranyl, isobenzofuranyl, benzothienyl, isobenzothienyl, quinolyl, isoquinolyl, quinoxalinyl, or quinazolinyl.

The term "perfluoroalkyl," as used herein, refers to a straight or branched aliphatic hydrocarbon chain of 1 to 6 carbon atoms and preferably 1 to 3 carbon atoms, in which all hydrogens are replaced with fluorine.

The term "alkanamido," as used herein, refers to the group R—C(=O)—NH— where R is an alkyl group of 1 to 5 carbon atoms.

The term "alkanoyl," as used herein, refers to the group R—C(=O)— where R is an alkyl group of 1 to 5 carbon atoms.

The term "alkanoyloxy," as used herein, refers to the group R—C(=O)—O— where R is an alkyl group of 1 to 5 carbon atoms.

The term "alkanesulfonamido," as used herein, refers to the group R—S(O)$_2$—NH— where R is an alkyl group of 1 to 6 carbon atoms.

The term "alkoxy," as used herein, refers to the group R—O— where R is an alkyl group of 1 to 6 carbon atoms.

The term "perfluoroalkoxy," as used herein, refers to the group R—O where R is a perfluoroalkyl group of 1 to 6 carbon atoms.

The terms "monoalkylamino" and "dialkylamino," as used herein, respectively refer to —NHR and —NRR$_a$, where R and R$_a$ are independently selected from an alkyl group of 1 to 6 carbon atoms.

The term "carboxamido," as used herein, refers to the group NH$_2$—C(=O)—.

The term "carboalkoxy," as used herein, refers to the group R—O—C(=O)— where R is an alkyl group of 1 to 5 carbon atoms.

The term "carboxy," as used herein, refers to the group —COOH.

The terms "halogen" or "halo," as used herein, refer to chlorine, bromine, fluorine or iodine.

The term "substituted," as used herein, refers to a moiety, such as an aryl, heteroaryl, cycloalkyl, heterocycloalkyl, or spirocyclic moiety having from 1 to about 5 substituents, and more preferably from 1 to about 3 substituents independently selected from a halogen, hydroxyl, alkyl of 1 to 6 carbon atoms, perfluoroalkyl of 1 to 6 carbon atoms, alkoxy of 1 to 6 carbon atoms, or perfluoroalkoxy of 1 to 6 carbon atoms. Preferred substituents are a halogen atom, a lower alkyl, a perfluoroalkyl of 1 to 3 carbon atoms, an alkoxy group of 1 to 3 carbon atoms or a perfluoroalkoxy of 1 to 3 carbon atoms.

The terms "effective amount" and "therapeutically effective amount," as used herein, refer to the amount of a compound of formula 1 that, when administered to a patient, is effective to at least partially treat a condition from which the patient is suffering from. Such conditions include, but are not limited to, schizophrenia, schizoaffective disorder, schizophreniform disorder, L-DOPA-induced psychosis, bipolar disorder, obesity, obsessive compulsive disorder, depression, panic disorder, sleep disorders, eating disorders, and epilepsy.

The term "pharmaceutically acceptable salts" or "pharmaceutically acceptable salt" refers to salts derived from treating a compound of formula 1 with an organic or inorganic acid such as, for example, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, or similarly known acceptable acids.

The term "patient," as used herein, refers to a mammal.

The terms "administer," "administering," or "administration," as used herein, refer to either directly administering a compound or composition to a patient, or administering a prodrug derivative or analog of the compound to the patient, which will form an equivalent amount of the active compound or substance within the patient's body.

The terms "treat" or "treating," as used herein, refers to partially or completely alleviating, inhibiting, preventing, ameliorating and/or relieving the condition.

The terms "suffer" or "suffering" as used herein refers to one or more conditions that a patient has been diagnosed with, or is suspected to have.

In certain embodiments, the invention relates to compounds of formula 1:

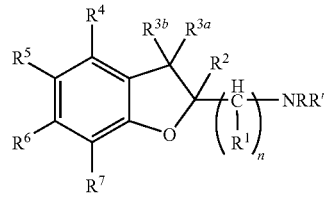

Formula 1 or pharmaceutically acceptable salts thereof;

wherein
R and R' are, independently, hydrogen, alkyl of 1 to 6 carbon atoms, cycloalkyl of 3 to 6 carbon atoms, or alkylcycloalkyl of 4 to 12 carbon atoms having 3 to 6 carbons in the cycloalkyl ring;
alternatively R and R' can be taken together with the nitrogen to which they are attached to form a ring containing 2-5 carbon atoms, wherein one of the ring carbon atoms is optionally replaced by nitrogen, sulfur or oxygen;
R$^1$ and R$^2$ are each, independently, hydrogen, alkyl of 1 to 6 carbon atoms, cycloalkyl of 3 to 6 carbon atoms, or perfluoroalkyl of 1 to 6 carbon atoms;
R$^{3a}$ and R$^{3b}$ are, independently, hydrogen, halogen, hydroxyl, alkyl of 1 to 6 carbon atoms, perfluoroalkyl of 1 to 6 carbon atoms, alkoxy of 1 to 6 carbon atoms, or perfluoroalkoxy of 1 to 6 carbon atoms;
two adjacent substituents selected from R$^4$ and R$^5$, or R$^5$ and R$^6$, or R$^6$ and R$^7$, together with the carbon atoms to which they are attached, form a cyclic moiety selected from a monocyclic cycloalkyl of 3 to 8 carbon atoms, a bridged cycloalkyl of 5 to 10 carbon atoms, a 3 to 8 membered heterocycloalkyl having 1 to 3 heteroatoms each independently selected from nitrogen, oxygen, or sulfur, aryl of 5 to 10 carbon atoms, or a 5 to 10 membered heteroaryl having 1 to 3 heteroatoms each independently selected from nitrogen, oxygen, or sulfur, wherein the monocyclic cycloalkyl or the heterocycloalkyl cyclic moiety may be optionally substituted at a single carbon atom with a cycloalkyl of 3 to 5 carbon atoms or a 3 to 5 membered heterocycloalkyl containing 1 or 2 heteroatoms each independently selected from nitrogen, oxygen, or sulfur, to form a spirocyclic group;
the remaining R$^4$ to R$^7$ substituents are, independently, hydrogen, halogen, cyano, hydroxyl, carboxyl, alkyl of 1 to 8 carbon atoms, perfluoroalkyl of 1 to 6 carbon atoms, alkoxy of 1 to 6 carbon atoms, perfluoroalkoxy of 1 to 6 carbon atoms, aryl of 5 to 10 carbon atoms, aryloxy of 5 to 10 carbon atoms, 5 to 10 membered heteroaryl having 1 to 3 heteroatoms each independently selected from nitrogen, oxygen or sulfur, alkenyl of 2 to 8 carbon atoms, alkanoyl of 2 to 6 carbon atoms, alkanoyloxy of 2 to 6 carbon atoms, carboalkoxy of 2 to 6 carbon atoms, carboxamido, alkanamido of 2 to 6 carbon atoms, alkanesulfonamido of 1 to 6 carbon atoms, amino, monoalkylamino of 1 to 6 carbon atoms, dialkylamino of 1 to 6 carbon atoms per alkyl moiety, cycloalkyl of 3 to 8 carbon atoms, or 3 to 8 membered heterocycloalkyl having 1 to 3 heteroatoms each independently selected from nitrogen, oxygen or sulfur; and n is 1, 2 or 3;

wherein any cycloalkyl or heterocycloalkyl group is saturated or partially saturated, and any aryl, heteroaryl, cycloalkyl, or heterocycloalkyl group may optionally be substituted with 1 to 5 substituents independently selected from halogen, hydroxyl, alkyl of 1 to 6 carbon atoms, perfluoroalkyl of 1 to 6 carbon atoms, alkoxy of 1 to 6 carbon atoms, or perfluoroalkoxy of 1 to 6 carbon atoms.

In certain other embodiments, the invention relates to compounds of formula 1 or pharmaceutically acceptable salts thereof;

wherein

R and R' are, independently, hydrogen, alkyl of 1 to 6 carbon atoms, or cycloalkyl of 3 to 6 carbon atoms;

alternatively R and R' can be taken together with the nitrogen to which they are attached to form a ring containing 2-5 carbon atoms, wherein one of the ring carbon atoms is optionally replaced by nitrogen, sulfur or oxygen;

$R^1$ and $R^2$ are each, independently, hydrogen, alkyl of 1 to 6 carbon atoms, cycloalkyl of 3 to 6 carbon atoms, or perfluoroalkyl of 1 to 6 carbon atoms;

$R^{3a}$ and $R^{3b}$ are, independently, hydrogen, halogen, hydroxyl, alkyl of 1 to 6 carbon atoms, perfluoroalkyl of 1 to 6 carbon atoms, alkoxy of 1 to 6 carbon atoms, or perfluoroalkoxy of 1 to 6 carbon atoms;

two adjacent substituents selected from $R^4$ and $R^5$, or $R^5$ and $R^6$, or $R^6$ and $R^7$, together with the carbon atoms to which they are attached, form a cyclic moiety selected from a monocyclic cycloalkyl of 3 to 8 carbon atoms, a bridged cycloalkyl of 5 to 10 carbon atoms, a 3 to 8 membered heterocycloalkyl having 1 to 3 heteroatoms each independently selected from nitrogen, oxygen, or sulfur, aryl of 5 to 10 carbon atoms, or a 5 to 10 membered heteroaryl having 1 to 3 heteroatoms each independently selected from nitrogen, oxygen, or sulfur;

the remaining $R^4$ to $R^7$ substituents are, independently, hydrogen, halogen, cyano, hydroxyl, carboxyl, alkyl of 1 to 8 carbon atoms, perfluoroalkyl of 1 to 6 carbon atoms, alkoxy of 1 to 6 carbon atoms, perfluoroalkoxy of 1 to 6 carbon atoms, alkenyl of 2 to 8 carbon atoms, alkanoyl of 2 to 6 carbon atoms, alkanoyloxy of 2 to 6 carbon atoms, carboalkoxy of 2 to 6 carbon atoms, carboxamido, alkanamido of 2 to 6 carbon atoms, alkanesulfonamido of 1 to 6 carbon atoms, amino, monoalkylamino of 1 to 6 carbon atoms, or dialkylamino of 1 to 6 carbon atoms per alkyl moiety; and n is 1, 2 or 3;

wherein any cycloalkyl or heterocycloalkyl group is saturated or partially saturated, and any aryl, heteroaryl, cycloalkyl, or heterocycloalkyl group may optionally be substituted with 1 to 5 substituents independently selected from halogen, hydroxyl, alkyl of 1 to 6 carbon atoms, perfluoroalkyl of 1 to 6 carbon atoms, alkoxy of 1 to 6 carbon atoms, or perfluoroalkoxy of 1 to 6 carbon atoms.

Other embodiments of the invention is directed to compounds of Formula 1 wherein n is 1, R' is hydrogen, and R, $R^1$ and $R^2$ are, independently, hydrogen, alkyl of 1 to 6 carbon atoms, or perfluoroalkyl of 1 to 6 carbon atoms.

In another embodiment, R, R', $R^1$, and $R^2$ of formula 1 are preferably each independently selected from hydrogen or alkyl of 1 to 6 carbon atoms and more preferably hydrogen.

In another embodiment, $R^{3a}$ and $R^{3b}$ are preferably each independently selected from hydrogen or alkyl of 1 to 3 carbon atoms and more preferably hydrogen.

In certain embodiments of the invention, the remaining (i.e., not fused) $R^4$ to $R^7$ susbtituents are each independently, hydrogen, halogen, alkyl of 1 to 8 carbon atoms, alkoxy of 1 to 6 carbon atoms, aryloxy of 5 to 10 carbon atoms, cycloalkyl of 3 to 8 carbon atoms, 3 to 8 membered heterocycloalkyl having 1 to 3 heteroatoms each independently selected from nitrogen, oxygen, and sulfur, aryl of 5 to 10 carbon atoms, or 5 to 10 membered heteroaryl having 1 to 3 heteroatoms each independently selected from nitrogen, oxygen, and sulfur.

In other embodiments of the invention, the remaining (i.e., not fused) $R^4$ to $R^7$ substituents are, independently, hydrogen, halogen, cyano, hydroxyl, carboxyl, alkyl of 1 to 8 carbon atoms, perfluoroalkyl of 1 to 6 carbon atoms, alkoxy of 1 to 6 carbon atoms, perfluoroalkoxy of 1 to 6 carbon atoms, alkenyl of 2 to 8 carbon atoms, alkanoyl of 2 to 6 carbon atoms, alkanoyloxy of 2 to 6 carbon atoms, carboalkoxy of 2 to 6 carbon atoms, carboxamido, alkanamido of 2 to 6 carbon atoms, alkanesulfonamido of 1 to 6 carbon atoms, amino, monoalkylamino of 1 to 6 carbon atoms, or dialkylamino of 1 to 6 carbon atoms per alkyl moiety, and more preferably hydrogen, halogen, hydroxyl, alkyl of 1 to 8 carbon atoms, perfluoroalkyl of 1 to 6 carbon atoms, alkoxy of 1 to 6 carbon atoms, or perfluoroalkoxy of 1 to 6 carbon atoms.

In certain other embodiments of the invention, $R^4$ and $R^5$ are, independently, hydrogen, halogen, alkyl of 1 to 8 carbon atoms, or alkoxy of 1 to 6 carbon atoms, and $R^6$ and $R^7$, together with the carbon atoms to which they are attached, form a monocyclic cycloalkyl of 3 to 8 carbon atoms, a bridged cycloalkyl of 5 to 10 carbon atoms, a 3 to 8 membered heterocycloalkyl having 1 to 3 heteroatoms each independently selected from nitrogen, oxygen, and sulfur, an aryl of 5 to 10 carbon atoms, or a 5 to 10 membered heteroaryl having 1 to 3 heteroatoms each independently selected from nitrogen, oxygen, and sulfur.

In further preferred embodiments of the invention, $R^6$ and $R^7$, together with the carbon atoms to which they are attached, form a bridged cycloalkyl of 5 to 10 carbon atoms, a monocyclic cycloalkyl of 3 to 8 carbon atoms, or an aryl of 5 to 10 carbon atoms optionally substituted with one to five substituents, each independently selected from alkyl, halogen, or alkoxy groups; $R^4$ and $R^5$ are, independently hydrogen, alkyl of 1 to 8 carbon atoms, alkoxy of 1 to 6 carbon atoms, or halogen; and R, $R^1$, and $R^2$ are each hydrogen or alkyl of 1 to 6 carbon atoms.

In certain other embodiments of the invention, $R^6$ and $R^7$, together with the carbon atoms to which they are attached, form a bridged cycloalkyl of 5 to 10 carbon atoms or a monocyclic cycloalkyl of 3 to 8 carbon atoms optionally substituted with one to three substituents, each independently selected from alkyl groups of 1 to 6 carbon atoms, halogens, or alkoxy groups of 1 to 6 carbon atoms; $R^4$ and $R^5$ are, independently, hydrogen, alkyl of 1 to 6 carbon atoms, alkoxy of 1 to 4 carbon atoms, or halogen; and R, $R^1$, and $R^2$ are each hydrogen.

In other embodiments of the invention, $R^6$ and $R^7$, together with the carbon atoms to which they are attached, form a bridged cycloalkyl group of five to eight carbon atoms optionally substituted with one to three substituents, each independently selected from alkyl groups of 1 to 6 carbon atoms, halogens, or alkoxy groups of 1 to 6 carbon atoms and $R^4$ and R⁵ are, independently, hydrogen, halogen, or alkyl of 1 to 4 carbon atoms and R, R¹, and R² are each hydrogen.

In other embodiments of the invention, R⁴ and R⁵, or R⁵ and R⁶, together with the carbon atoms to which they are attached, form a bridged cycloalkyl of 5 to 10 carbon atoms or a monocyclic cycloalkyl of 3 to 8 carbon atoms optionally substituted with one to three substituents, each independently selected from alkyl groups of 1 to 6 carbon atoms, halogens, or alkoxy groups of 1 to 6 carbon atoms and R⁴ and R⁵ are, independently, hydrogen, halogen, alkoxy of 1 to 4 carbon atoms or alkyl of 1 to 6 carbon atoms and R, R¹, and R² are each hydrogen.

Preferred aryl groups include phenyl and napthyl, and preferred heteroaryl groups include thienyl, furyl, pyrrolyl, imidazolyl, pyrazolyl, oxazolyl, isoxazolyl, thiazolyl, isothiazolyl, pyridyl, pyrazinyl, pyrimidinyl, pyridazinyl, indolyl, indazolyl, benzofuranyl, isobenzofuranyl, benzothienyl, isobenzothienyl, quinolyl, isoquinolyl, quinoxalinyl, and quinazolinyl.

Preferred heterocycloalkyl groups include pyrrolidinyl, imidazolidinyl, pyrazolidinyl, tetrahydrofuranyl, 1,3-dioxolanyl, 1,2-dioxolanyl, tetrahydrothiophen-yl, 1,3-dithiolanyl, 1,2-dithiolanyl, piperidinyl, piperazinyl, hexahydropyrimidinyl, hexahydropyridazinyl, tetrahydropyranyl, 1,4-dioxanyl, 1,3-dioxanyl, 1,2-dioxanyl, tetrahydropyranyl, 1,4-dithianyl, 1,3-dithianyl, 1,2-dithianyl, thiazolidinyl, oxazolidinyl, 1,3-oxathiolanyl, isoxazolidinyl, 1,2-oxathiolanyl, thiomorpholinyl, morpholinyl, 1,4-oxathianyl, 1,3-thiazinanyl, 1,3-oxazinanyl, 1,3-oxathianyl, 1,2-thiazinanyl, 1,2-oxazinanyl, and 1,2-oxathianyl.

In still further preferred embodiments of the invention, the compounds of formula 1 are:
(±)-1-(3,6,7,8-tetrahydro-2H-indeno[4,5-b]furan-2-yl)methanamine,
(+)-1-(3,6,7,8-tetrahydro-2H-indeno[4,5-b]furan-2-yl)methanamine,
(−)-1-(3,6,7,8-tetrahydro-2H-indeno[4,5-b]furan-2-yl)methanamine,
(±)-1-(2,3,6,7,8,9-hexahydronaphtho[1,2-b]furan-2-yl)methanamine,
(+)-1-(2,3,6,7,8,9-hexahydronaphtho[1,2-b]furan-2-yl)methanamine,
(−)-1-(2,3,6,7,8,9-hexahydronaphtho[1,2-b]furan-2-yl)methanamine,
(±)-1-(5-methyl-3,6,7,8-tetrahydro-2H-indeno[4,5-b]furan-2-yl)methanamine,
(+)-1-(5-methyl-3,6,7,8-tetrahydro-2H-indeno[4,5-b]furan-2-yl)methanamine,
(−)-1-(5-methyl-3,6,7,8-tetrahydro-2H-indeno[4,5-b]furan-2-yl)methanamine,
(±)-1-(2,3-dihydronaphtho[1,2-b]furan-2-yl)methanamine,
(+)-1-(2,3-dihydronaphtho[1,2-b]furan-2-yl)methanamine,
(−)-1-(2,3-dihydronaphtho[1,2-b]furan-2-yl)methanamine,
(±)-1-(2,3,5,6,7,8-hexahydronaphtho[2,3-b]furan-2-yl)methanamine,
(±)-1-(1,2,6,7,8,9-hexahydronaphtho[2,1-b]furan-2-yl)methanamine,
(9-methoxy-4-oxatetracyclo[9.2.1.0²,¹⁰.0³,⁷]tetradeca-2,7,9-trien-5-yl)methylamine,
(±)-1-(5-methoxy-2,3,6,7,8,9-hexahydro-6,9-ethanonaphtho[1,2-b]furan-2-yl)methanamine,
(+)-1-(5-methoxy-2,3,6,7,8,9-hexahydro-6,9-ethanonaphtho[1,2-b]furan-2-yl)methanamine,
(−)-1-(5-methoxy-2,3,6,7,8,9-hexahydro-6,9-ethanonaphtho[1,2-b]furan-2-yl)methanamine,
(2R*)-1-[(2R*)-3,6,7,8-tetrahydro-2H-indeno[4,5-b]furan-2-yl]ethylamine,
(±)-1-(5-chloro-2,3-dihydronaphtho[1,2-b]furan-2-yl)methanamine,
(±)-1-(5-chloro-2,3-dihydronaphtho[1,2-b]furan-2-yl)-N-methylmethanamine,
(±)-1-(4-chloro-3,6,7,8-tetrahydro-2H-indeno[4,5-b]furan-2-yl)methanamine,
(−)-1-(4-chloro-3,6,7,8-tetrahydro-2H-indeno[4,5-b]furan-2-yl)methanamine,
(+)-1-(4-chloro-3,6,7,8-tetrahydro-2H-indeno[4,5-b]furan-2-yl)methanamine,
(±)-1-(4-chloro-3,6,7,8-tetrahydro-2H-indeno[4,5-b]furan-2-yl)-N-methylmethanamine,
(±)-1-(5-chloro-3,6,7,8-tetrahydro-2H-indeno[4,5-b]furan-2-yl)methanamine,
(−)-1-(5-chloro-3,6,7,8-tetrahydro-2H-indeno[4,5-b]furan-2-yl)methanamine, or
(+)-1-(5-chloro-3,6,7,8-tetrahydro-2H-indeno[4,5-b]furan-2-yl)methanamine.

The compounds of formula 1 have affinity for and agonist or partial agonist activity at the 2c subtype of brain serotonin receptors and are thus of interest for the treatment of mental disorders, including psychotic disorders such as schizophrenia including paranoid type, disorganized type, catatonic type, and undifferentiated type, schizophreniform disorder, schizoaffective disorder, delusional disorder, substance-induced psychotic disorder, and psychotic disorder not otherwise specified; L-DOPA-induced psychosis; psychosis associated with Alzheimer's dementia; psychosis associated with Parkinson's disease; psychosis associated with Lewy body disease; bipolar disorders such as bipolar I disorder, bipolar II disorder, and cyclothymic disorder; depressive disorders such as major depressive disorder, dysthymic disorder, substance-induced mood disorder, and depressive disorder not otherwise specified; mood episodes such as major depressive episode, manic episode, mixed episode, and hypomanic episode; anxiety disorders such as panic attack, agoraphobia, panic disorder, specific phobia, social phobia, obsessive compulsive disorder, posttraumatic stress disorder, acute stress disorder, generalized anxiety disorder, separation anxiety disorder, substance-induced anxiety disorder, and anxiety disorder not otherwise specified; adjustment disorders such as adjustment disorders with anxiety and/or depressed mood; intellectual deficit disorders such as dementia, Alzheimer's disease, and memory deficit; eating disorders (e.g., hyperphagia, bulimia or anorexia nervosa) and combinations of these mental disorders that may be present in a mammal. For example, mood disorders such as depressive disorders or bipolar disorders often accompany psychotic disorders such as schizophrenia. A more complete description of the aforementioned mental disorders can be found in the Diagnostic and Statistical Manual of Mental Disorders, 4th edition, Washington, D.C., American Psychiatric Association (1994), incorporated herein by reference in its entirety.

The compounds of formula 1 are also of interest for the treatment of epilepsy; migraines; sexual dysfunction; sleep disorders; substance abuse, including addiction to alcohol and various drugs, including cocaine and nicotine; gastrointestinal disorders, such as malfunction of gastrointestinal motility; and obesity, with its consequent comorbidities including Type II diabetes, cardiovascular disease, hypertension, hyperlipidemia, stroke, osteoarthritis, sleep apnea, gall bladder disease, gout, some cancers, some infertility, and early mortality. The compounds of formula 1 can also be used to treat central nervous system deficiencies associated, for example, with trauma, stroke, and spinal cord injuries. The compounds of formula 1 can therefore be used to improve or inhibit further degradation of central nervous system activity during or following the malady or trauma in question. Included in these improvements are maintenance or improvement in motor and motility skills, control, coordination and strength.

In certain embodiments, the present invention therefore provides methods of treating, including, preventing, inhibiting or alleviating each of the maladies listed above in a mammal, preferably in a human, the methods comprising administering a therapeutically effective amount of a compound of formula 1 to a patient suspected to suffer from such a malady.

In other embodiments, the invention relates to compositions comprising at least one compound of formula 1, or a stereoisomer or pharmaceutically acceptable salt thereof, and one or more pharmaceutically acceptable carriers, excipients, or diluents. Such compositions include pharmaceutical compositions for treating or controlling disease states or conditions of the central nervous system. In certain embodiments, the compositions comprise mixtures of one or more compounds of formula 1.

Certain of the compounds of formula 1 contain stereogenic carbon atoms or other chiral elements and thus give rise to stereoisomers, including enantiomers and diastereomers. In preferred embodiments, this invention relates to all of the stereoisomers of the 1-(2,3-dihydro-1-benzofuran-2-yl)alkanamine derivatives, as well as to mixtures of the stereoisomers. Throughout this application, the name of the product, where the absolute configuration of an asymmetric center is not indicated, is intended to embrace the individual stereoisomers as well as mixtures of stereoisomers. When it is necessary to distinguish the enantiomers from one another and from the racemate, the sign of the optical rotation [(+), (−) and (±)] is utilized. Furthermore, throughout this application, the designations R* and S* are used to indicate relative stereochemistry, employing the Chemical Abstracts convention which automatically assigns R* to the lowest numbered asymmetric center.

Where an enantiomer is preferred, it may, in some embodiments, be provided substantially free of the corresponding enantiomer. Thus, an enantiomer substantially free of the corresponding enantiomer refers to a compound that is isolated or separated via separation techniques or prepared free of the corresponding enantiomer. "Substantially free," as used herein, means that the compound is made up of a significantly greater proportion of one enantiomer. In preferred embodiments, the compound is made up of at least about 90% by weight of a preferred enantiomer. In other embodiments of the invention, the compound is made up of at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein. Methods for the preparation of preferred enantiomers are described, for example, in Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972), each of which is hereby incorporated by reference in its entirety.

This invention also provides processes for preparing a compound of formula 1 or a pharmaceutically acceptable salt thereof which processes include one of the following:

a) reacting a compound of formula 7

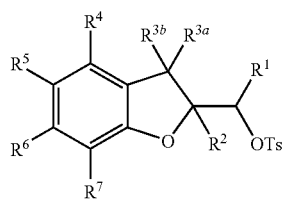

7 wherein $R^1$, $R^2$, $R^3$, $R^4$, $R^5$, $R^6$, and $R^7$ are as defined in claim 1, with sodium azide and reducing the product to give a compound of formula 1 wherein n is 1 and R and R' are both H; or b) reacting a compound of formula 7 as defined above with an amine of formula NHRR' where R and R' are as defined in claim 1 to give a corresponding compound of formula 1 wherein n is 1; or c) reacting a compound of formula 7 as defined above with sodium cyanide followed by reduction to give a compound of formula 1 wherein n is 2 and R and R' are both H;

d) converting a compound of formula 1 as defined in claim 1 to a pharmaceutically acceptable salt or vice versa; or e) isolating a specific enantiomer or diastereomer of a compound of formula 1 or a pharmaceutically acceptable salt thereof as defined in claim 1 from a mixture thereof.

The 1-(2,3-dihydro-1-benzofuran-2-yl)alkanamine derivatives of formula 1 can be prepared as illustrated in Scheme I.

Scheme I

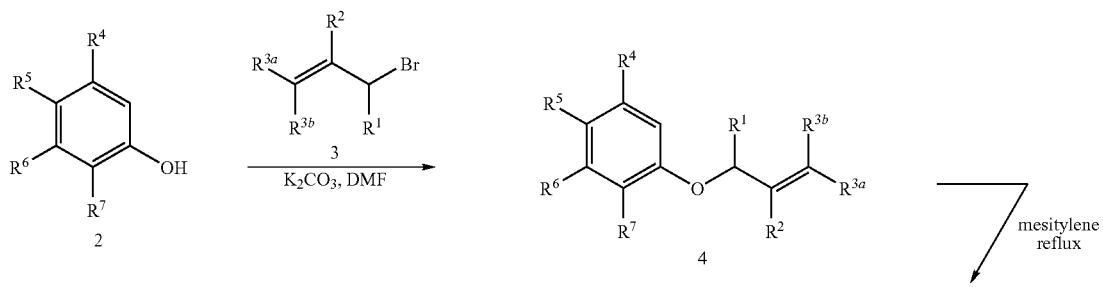

-continued

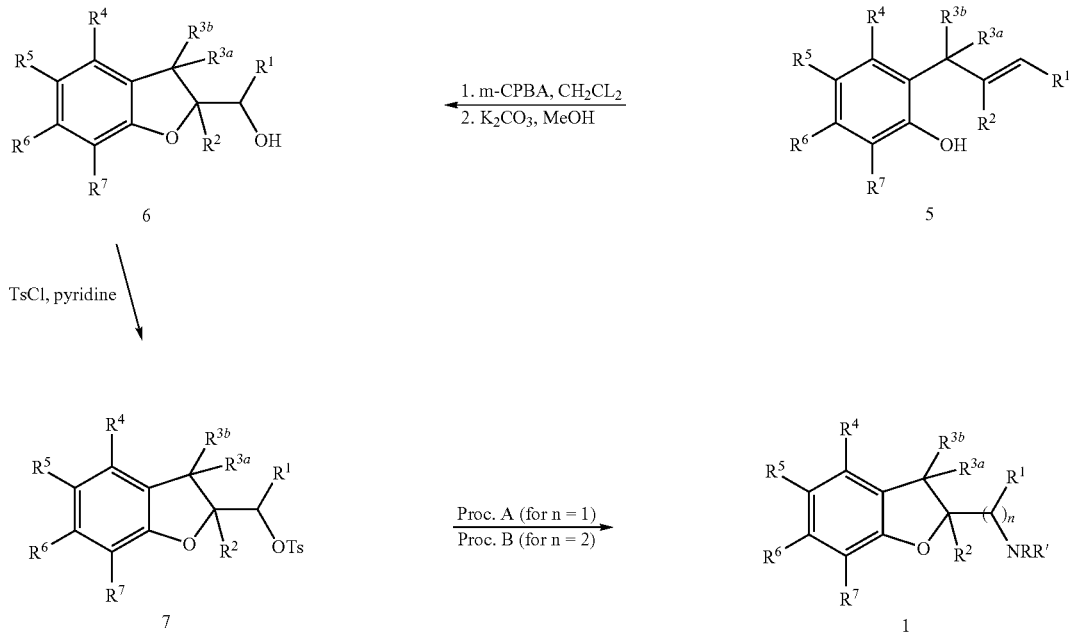

Proc. A: 1. a) NaN3, DMSO and b) reduction, or 2. NHRR'/DMSO
Proc. B: 1. a) NaCN/DMSO and b) H₂/5% Rh on Al₂O₃, NH₄OH Variables used are as defined for Formula 1, unless otherwise noted. The appropriately substituted phenyl (2) is alkylated with an appropriately substituted allyl bromide and a suitable base such as potassium carbonate in a solvent such as N,N-dimethylformamide. Alternatively, the phenyl (2) may be alkylated with an appropriately substituted alcohol (3) utilizing Mitsunobu conditions. The phenyls, allyl bromides, and allyl alcohols appropriate for the synthesis of the compounds of formula 1 are either commercially available or can readily be prepared by one skilled in the art. The resulting allyl ether (4) is treated in refluxing mesitylene or other suitable high boiling solvent to afford the desired Claisen rearrangement product. The 2-allyl phenyl (5) represents an intermediate in which epoxidation of the double bond with 3-chloroperoxybenzoic acid in dichloromethane is followed by treatment of the resulting epoxy phenyl intermediate with a suitable base, such as potassium carbonate, in a solvent such as methanol, to induce cyclization to give the 2,3-dihydro-1-benzofuran-2-yl)methanol (6). Treatment of (6) with p-toluenesulfonyl chloride and a suitable base such as pyridine affords the tosylate (7). Conversion of (7) to the amine (1) can be accomplished by treatment with sodium azide in a solvent such as dimethylsulfoxide followed by reduction of the azide, or by direct treatment with an appropriately substituted amine to provide the compounds of formula (1) in which n=1. Alternatively, displacement of tosylate (7) with sodium cyanide in DMSO followed by catalytic reduction of the corresponding nitrile provides the primary amines of formula (1) wherein n=2. Subsequent reaction with the appropriate alkyl or cycloalkyl may be used to generate the secondary or tertiary amines.

Additionally, the compounds of formula 1 can be prepared in a stereoselective manner as illustrated in Scheme II.

Scheme II

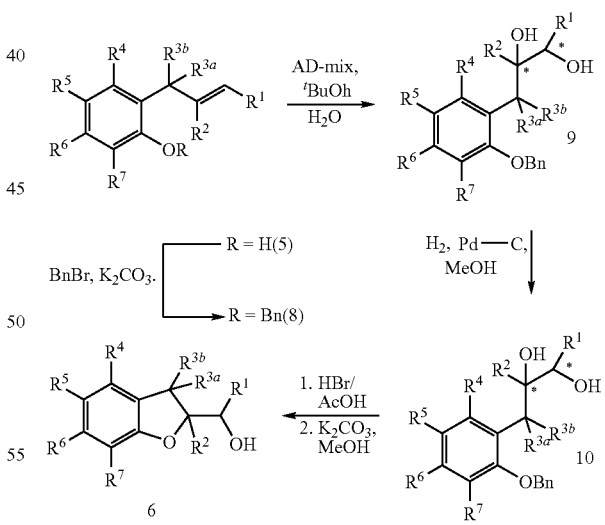

Protection of the phenyl (5) with a suitable protecting group, such as benzyl, by treatment with benzyl bromide and a suitable base, such as potassium carbonate, in a solvent such as N,N-dimethylformamide gives the benzyl ether (8). Treatment of (8) utilizing extant methodology known to one skilled in the art for the stereoselective oxidation of double bonds, such as the Sharpless Asymmetric Dihydroxylation (A-D), provides the diol (9) in stereochemically enriched form. There are many methods available to one skilled in the art for the transfer of the stereochemical information present in (9) into the compounds of formula (1) with retention of stereochemical integrity. One such method involves deprotection of the benzyl ether with catalytic palladium on carbon under a hydrogen atmosphere (45 psi) in a solvent such as methanol to provide triol (10). Formation to the previously described 2,3-dihydro-1-benzofuran-2-yl)methanol (6) can be accomplished by treatment of (9) with hydrogen bromide in acetic acid to provide the intermediate vicinal acetoxy bromide followed by cyclization with a suitable base such as potassium carbonate in a solvent such as methanol.

Alternatively, the compounds of formula 1 can be prepared via selective mono-protection of diol (9) with a suitable protecting group as illustrated in Scheme III.

sunobu conditions, such as triphenylphosphine, in the presence of diethylazodicarboxylate in a solvent such as toluene provides the 2,3-dihydro-1-benzofuran-2-yl)methanol (13) protected as the silyl ether. Removal of the silyl ether in (13) using standard conditions such as tetrabutylamonnium fluoride in a solvent such as tetrahydrofuran then provides the alcohol (6), which can be converted to the compounds of formula 1 as previously described (Scheme I).

In lieu of a protecting group, diol (9) can be converted to the mono-tosylated derivative (12a) by treatment with p-toluenesulfonyl chloride and a suitable base such as pyridine to give the desired product as illustrated in Scheme IV.

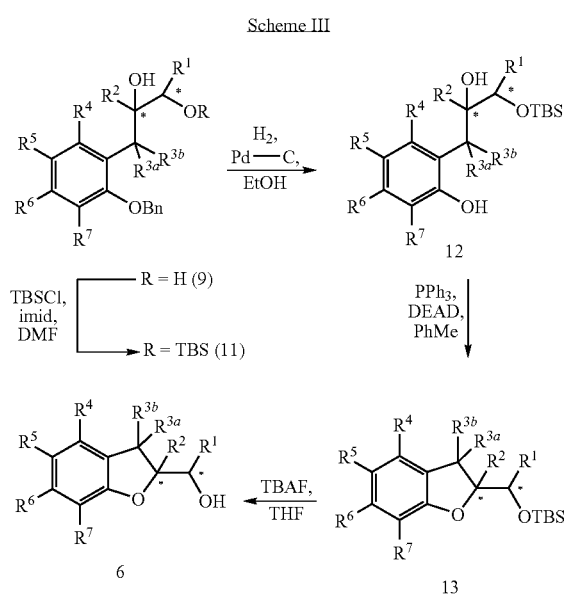

Scheme III

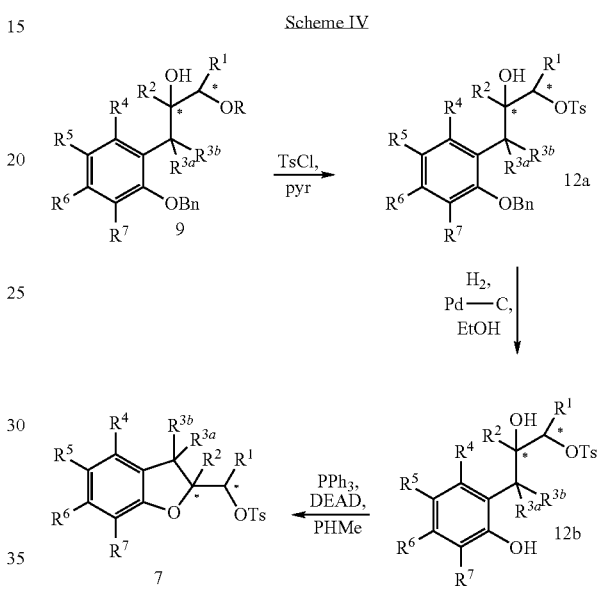

Scheme IV

Treatment of (9) with tert-butyldimethylsilyl chloride in the presence of a suitable base such as imidazole in a solvent such as N,N,-dimethylformamide followed by deprotection of the benzyl ether, as previously described, with catalytic palladium on carbon under a hydrogen atmosphere gives phenyl (12). Cyclodehydration of (12) using standard Mit- Deprotection of the benzyl ether with catalytic palladium on carbon gives phenyl (12b) followed by cyclodehydration with triphenylphosphine in the presence of diethylazodicarboxylate as previously described provides the aforementioned 2,3-dihydro-1-benzofuran-2-yl)methyl 4-methylbenzenesulfonate (7).

An additional route to the production of stereochemically enriched compounds of formula 1 is illustrated in Scheme V.

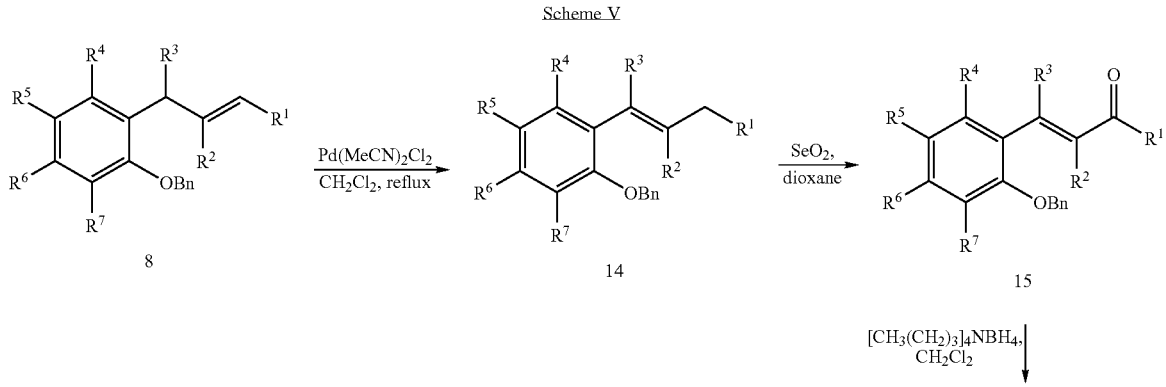

Scheme V

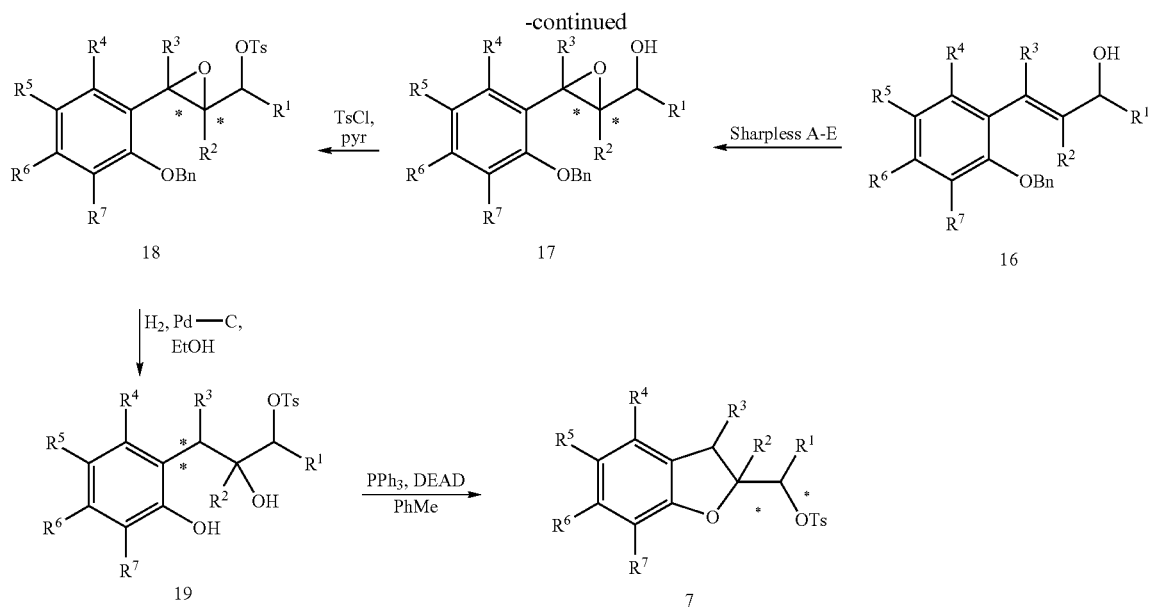

Palladium or transition metal catalyzed transposition of the double bond present in the previously described 2-allyl benzyl ether (8) using an appropriate catalyst such as dichlorobis(acetonitrile)palladium(II) in dichloromethane provides the styrene derivative (14). Treatment of (14) with selenium dioxide in dioxane provides the carbonyl derivative (15). Reduction of the carbonyl to the allylic alcohol (16) can be accomplished by treatment with an appropriate reducing agent such as tetrabutylammonium borohydride in a solvent such as dichloromethane. The allylic alcohol (16) provides a suitable intermediate for the stereoselective introduction of oxygenation that permits transfer of this stereochemical integrity into the compounds of formula (1). The Sharpless Asymmetric Epoxidation (A-E) reaction is a general method for the stereoselective epoxidation of allylic alcohols, and treatment of (16) under the appropriate conditions provides epoxy alcohol (17) with a high degree of stereoselectivity. The alcohol present in (17) can then be tosylated with p-toluenesulfonyl chloride as previously described to give derivative (18). Deprotection of the benzyl ether with concomitant regioselective opening of the epoxide, maintaining the stereochemical information introduced by the Sharpless A-E, is accomplished under the appropriate conditions by treatment of (18) with palladium on carbon under a hydrogen atmosphere in a solvent such as ethanol.

Cyclodehydration using Mitsunobu Conditions as Previously Described then Affords 2,3-dihydro-1-benzofuran-2-yl)methyl 4-methylbenzenesulfonate (7).

In certain embodiments, the invention relates to compositions comprising at least one compound of formula 1, or a stereoisomer or pharmaceutically acceptable salt thereof, and one or more pharmaceutically acceptable carriers, excipients, or diluents. Such compositions are prepared in accordance with acceptable pharmaceutical procedures, such as, for example, those described in *Remingtons Pharmaceutical Sciences*, 17th edition, ed. Alfonoso R. Gennaro, Mack Publishing Company, Easton, Pa. (1985), which is incorporated herein by reference in its entirety. Pharmaceutically acceptable carriers are those carriers that are compatible with the other ingredients in the formulation and are biologically acceptable.

The compounds of formula 1 can be administered orally or parenterally, neat, or in combination with conventional pharmaceutical carriers. Applicable solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers can be used in preparing solutions, suspensions, emulsions, syrups and elixirs. The active ingredient can be dissolved or suspended in a pharmaceutically acceptable liquid carrier such as water, an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form.

The compounds of formula 1 can be administered rectally or vaginally in the form of a conventional suppository. For administration by intranasal or intrabronchial inhalation or insufflation, the compounds of formula 1 can be formulated into an aqueous or partially aqueous solution, which can then be utilized in the form of an aerosol. The compounds of formula 1 can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of formula 1 are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age, and response pattern of the patient. The treatment of substance abuse follows the same method of subjective drug administration under the guidance of the attending physician. The usual daily dose depends on the specific compound, method of treatment and condition treated. The usual daily dose is 0.01-1000 mg/kg for oral application, preferably 0.5-500 mg/kg, and 0.1-100 mg/kg for parenteral application, preferably 0.5-50 mg/kg. The compounds can be administered orally, rectally, parenterally, or topically to the skin and mucosa.

In certain embodiments, the present invention is directed to prodrugs of compounds of formula 1. The term "prodrug," as used herein, means a compound that is convertible in vivo by metabolic means (e.g. by hydrolysis) to a compound of formula 1. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., Journal of Drug Delivery Reviews, 8:1-38(1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is hereby incorporated by reference in its entirety.

Intermediate 1

5-allyl-2,3-dihydro-1H-inden-4-yl Benzyl Ether

To a suspension of potassium carbonate (23.49 g, 0.170 mol) in N,N-dimethylformamide (350 mL) was added indan-4-ol (7.60 g, 0.057 mol) followed by allyl bromide (8.22 g, 0.068 mol) and the reaction mixture was allowed to stir at room temperature for 12 h. The reaction mixture was diluted with water (1000 mL) to dissolve any solids and extracted with diethyl ether (3×250 mL). The combined organic layers were washed with water (4×500 mL), aqueous sodium chloride (400 mL), dried (magnesium sulfate) and the solvent was removed in vacuo to give 4-(allyloxy)indane. The allyl ether was dissolved in mesitylene (40 mL) and heated at reflux for 8 h. Removal of the solvent in vacuo provided 5-allylindan-4-ol, which was re-dissolved in N,N-dimethylformamide (250 mL). Potassium carbonate (14.28 g, 0.103 mol), benzyl bromide (6.48 g, 0.038 mol), and tetrabutylammonium iodide (2.54 g, 0.007 mol) were added to the reaction mixture. The reaction mixture was allowed to stir at room temperature for 12 h. The reaction mixture was diluted with water (1000 mL) to dissolve any solids and extracted with diethyl ether (3×250 mL). The combined organic layers were washed with water (4×500 mL), aqueous sodium chloride (400 mL), dried (magnesium sulfate) and the solvent was removed in vacuo to give a crude oil. Purification by flash column chromatography (silica, ethyl acetate:hexanes 1:9) provided 10.22 g (68%) of 5-allyl-2,3-dihydro-1H-inden-4-yl benzyl ether as a pale yellow oil. $R_f$=0.45 (silica, ethyl acetate:hexanes 1:19); Anal. calcd. for $C_{19}H_{20}O$: C, 86.32; H, 7.63. Found: C, 85.90; H, 7.49.

Intermediate 2

(±)-3-[4-(benzyloxy)-2,3-dihydro-1H-inden-5-yl]propane-1,2-diol

To a suspension of AD-mix-α (53.00 g) in water (200 mL) at 0° C. was slowly added a solution of 5-allyl-2,3-dihydro-1H-inden-4-yl benzyl ether (10.00 g, 37.8 mmol) in tert-butyl alcohol (200 mL) and the reaction mixture was allowed to stir at room temperature for 12 h. The reaction mixture was quenched by the addition of sodium hydrogen sulfite and diluted with water (500 mL) and ethyl acetate (400 mL). The aqueous phase was extracted with ethyl acetate (3×200 mL) and the combined organic extracts were washed with water (2×250 mL), aqueous sodium chloride (400 mL), dried (magnesium sulfate), and the solvent was removed in vacuo to give a crude oil. Purification by flash column chromatography (silica, ethyl acetate:hexanes 1:1) gave 9.10 g (91%, 31% ee) of (±)-3-[4-(benzyloxy)-2,3-dihydro-1H-inden-5-yl]propane-1,2-diol as a colorless oil. $R_f$=0.3 (silica, ethyl acetate: hexanes 1:1); Anal. calcd. for $C_{19}H_{22}O_3$: C, 76.48; H, 7.43. Found: C, 76.14; H, 7.52.

Intermediate 3

(±)-1-[4-(benzyloxy)-2,3-dihydro-1H-inden-5-yl]-3-{[tert-butyl(dimethyl)silyl]oxy}propan-2-ol To a solution of (±)-3-[4-(benzyloxy)-2,3-dihydro-1H-inden-5-yl]propane-1,2-diol (9.10 g, 30.5 mmol) in N,N-dimethylformamide (150 mL) was added tert-butyldimethylsilyl chloride (4.83 g, 32.04 mmol) followed by imidazole (2.49 g, 36.60 mmol) and the reaction mixture was allowed to stir at room temperature overnight. The reaction mixture was quenched with methanol (5 mL) and diluted with diethyl ether (500 mL). The organic layer was washed with aqueous hydrogen chloride (200 mL, 0.5 N), water (3×200 mL), saturated aqueous sodium chloride (200 mL), dried (magnesium sulfate) and the solvent was removed in vacuo to provide a crude oil. Purification by flash column chromatography (silica, ethyl acetate:hexanes 1:4) gave 9.20 g (73%) of (±)-1-[4-(benzyloxy)-2,3-dihydro-1H-inden-5-yl]-3-{[tert-butyl (dimethyl)silyl]oxy}propan-2-ol as a colorless oil. $R_f$=0.37 (silica, ethyl acetate:hexanes 1:4); Anal. calcd. for $C_{25}H_{36}O_3Si$: C, 72.77; H, 8.79. Found: C, 72.3; H, 8.48.

Intermediate 4

(±)-5-(3-{[tert-butyl(dimethyl)silyl]oxy}-2-hydroxypropyl)indan-4-ol

To a solution of (±)-1-[4-(benzyloxy)-2,3-dihydro-1H-inden-5-yl]-3-{[tert-butyl(dimethyl)silyl]oxy}propan-2-ol (9.20 g, 22.29 mmol) in ethanol (200 mL) was added palladium on carbon (1.00 g, 10 wt. %) and the reaction mixture was shaken under an $H_2$ atmosphere (50 psi) for 4 h. The reaction mixture was filtered (celite) and the solvent was removed in vacuo to provide a crude oil. Purification by flash column chromatography (silica, ethyl acetate:hexanes 1:6) gave 6.78 g (94%) of (±)-5-(3-{[tert-butyl(dimethyl)silyl] oxy}-2-hydroxypropyl)indan-4-ol as a colorless oil. $R_f$=0.47 (silica, ethyl acetate:hexanes 1:3); Anal. calcd. for $C_{18}H_{30}O_3Si$: C, 67.03; H, 9.38. Found: C, 66.01; H, 9.33.

Intermediate 5

(±)-tert-butyl(dimethyl)(3,6,7,8-tetrahydro-2H-indeno[4,5-b]furan-2-ylmethoxy)silane To a solution of (±)-5-(3-{[tert-butyl(dimethyl)silyl]oxy}-2-hydroxypropyl)indan-4-ol (6.78 g, 21.02 mmol) in tetrahydrofuran (210 mL) cooled to 0° C. was added triphenylphosphine (5.79 g, 22.07 mmol) followed by diethylazodicarboxylate (3.84 g, 22.07 mmol) and the reaction mixture was allowed to stir at room temperature overnight. The reaction mixture was quenched by the addition of water (10 mL) and the solvent was removed in vacuo to give a crude solid. Purification by flash column chromatography (silica, ethyl acetate:hexanes 1:7) provided 2.93 g (46%) of (±)-tert-butyl(dimethyl)(3,6,7,8-tetrahydro-2H-indeno[4,5-b]furan-2-ylmethoxy)silane as a colorless oil. $R_f$=0.86 (silica, ethyl acetate:hexanes 1:5); Anal. calcd. for $C_{18}H_{28}O_2Si$: C, 71.0; H, 9.27. Found: C, 69.77; H, 9.21.

Intermediate 6

(±)-3,6,7,8-tetrahydro-2H-indeno[4,5-b]furan-2-ylmethanol

To a solution of (±)-tert-butyl(dimethyl)(3,6,7,8-tetrahydro-2H-indeno[4,5-b]furan-2-ylmethoxy)silane (2.93 g; 9.62 mmol) in tetrahydrofuran (100 mL) cooled to 0° C. was added tetrabutylammonium fluoride (10.6 mL, 1.0 M solution in tetrahydrofuran) and the reaction mixture was allowed to stir at room temperature for 8 h. The reaction mixture was diluted with water (200 mL) and extracted with ethyl acetate (2×150 mL). The combined organic extracts were washed with saturated aqueous sodium chloride (400 mL), dried (magnesium sulfate) and the solvent was removed in vacuo to give a crude oil. Purification by flash column chromatography (silica, ethyl acetate:hexanes 1:3) afforded 1.67 g (91%) of (±)-3,6,7,8-tetrahydro-2H-indeno[4,5-b]furan-2-ylmethanol as a colorless oil. $R_f$=0.63 (silica, ethyl acetate:hexanes 1:2); Anal. calcd. for $C_{12}H_{14}O_2$: C, 75.76; H, 7.42. Found: C, 74.46; H, 7.44.

Intermediate 7

(±)-benzyl 3,6,7,8-tetrahydro-2H-indeno[4,5-b]furan-2-ylmethylcarbamate

To a solution of (±)-1-(3,6,7,8-tetrahydro-2H-indeno[4,5-b]furan-2-yl)methanamine (0.568 g, 3.00 mmol) in tetrahydrofuran (30 mL) cooled to 0° C. was added diisopropylethylamine (0.427 g, 3.30 mmol) followed by benzyl chloroformate (0.538 g, 3.15 mmol) and the reaction mixture was allowed to stir at 0° C. for 1 h. The reaction mixture was quenched by the addition of saturated aqueous ammonium chloride (100 mL) and extracted with diethyl ether (2×150 mL). The combined organic extracts were washed with saturated aqueous sodium chloride (100 mL), dried (magnesium sulfate), and the solvent was removed in vacuo to provide a crude oil. Purification by flash column chromatography (silica, ethyl acetate:hexanes 1:9) afforded 0.663 g (68%) of (±)-benzyl 3,6,7,8-tetrahydro-2H-indeno[4,5-b]furan-2-ylmethylcarbamate as a white solid. $R_f$=0.30 (silica, ethyl acetate:hexanes 1:9); mp 99-101° C.; Anal. calcd. for $C_{20}H_{21}NO_3$: C, 74.28; H, 6.55; N, 4.33. Found: C, 73.82; H, 6.53; N, 4.25. Chiral HPLC separation of (±)-benzyl 3,6,7,8-tetrahydro-2H-indeno[4,5-b]furan-2-ylmethylcarbamate (Chiralcel OJ, isopropanol:hexane 7:3) provided two fractions. Fraction 1 ($R_t$=13.237 min, Chiralcel OJ, isopropanol: hexanes 3:7); Fraction 2 ($R_t$=16.526 min, Chiralcel OJ, isopropanol:hexanes 3:7).

Intermediate 8

2-allyl-5,6,7,8-tetrahydronaphthalen-1-yl benzyl ether

Treatment of 2-allyl-5,6,7,8-tetrahydronaphthalen-1-ol (18.48 g, 0.098 mol) with potassium carbonate (41.46 g, 0.300 mol), benzyl bromide (18.81 g, 0.110 mol), and tetrabutylammonium iodide (7.39 g, 0.020 mol) generally according to the procedure described for Intermediate 1 afforded 24.05 g (88%) of 2-allyl-5,6,7,8-tetrahydronaphthalen-1-yl benzyl ether as a pale yellow oil. $R_f$=0.39 (silica, ethyl acetate:hexanes 1:19); Anal. calcd. for $C_{20}H_{22}O0.2H_2O$: C, 85.19; H, 8.01. Found: C, 84.95; H, 7.75.

Intermediate 9

(±)-3-[1-(benzyloxy)-5,6,7,8-tetrahydronaphthalen-2-yl]propane-1,2-diol

Treatment of 2-allyl-5,6,7,8-tetrahydronaphthalen-1-yl benzyl ether (11.02 g, 0.040 mol) with AD-mix-α (55.42 g) generally according to the procedure described for Intermediate 2 gave 9.6 g (78%, 32% ee) of (±)-3-[1-(benzyloxy)-5,6,7,8-tetrahydronaphthalen-2-yl]propane-1,2-diol as a colorless oil. $R_f$=0.42 (silica, ethyl acetate:hexanes 1:1); Anal. calcd. for $C_{20}H_{24}O.0.5H_2O$: C, 74.74; H, 7.84. Found: C, 74.39; H, 7.60.

Intermediate 10

(±)-1-[1-(benzyloxy)-5,6,7,8-tetrahydronaphthalen-2-yl]-3-{[tert-butyl(dimethyl)silyl]oxy}propan-2-ol Treatment of (±)-3-[1-(benzyloxy)-5,6,7,8-tetrahydronaphthalen-2-yl]propane-1,2-diol (9.6 g, 0.031 mol) with tert-butyldimethylsilyl chloride (4.86 g, 0.032 mol) and imidazole (2.51 g, 0.037 mol) generally according to the procedure described for Intermediate 3 afforded 7.93 g (61%) of (±)-1-[1-(benzyloxy)-5,6,7,8-tetrahydronaphthalen-2-yl]-3-{[tert-butyl(dimethyl)silyl]oxy}propan-2-ol as a colorless oil. $R_f$=0.63 (silica, ethyl acetate:hexanes 1:3); $^1$H NMR (DMSO-$d_6$) $\delta_H$ 7.48 (d, 2H); 7.35 (m, 3H); 7.03 (d, 1H); 6.78 (d, 1H); 4.77 (q, 2H); 4.55 (d, 1H); 3.75 (m, 1H); 3.45 (m, 2H); 2.85 (dd, 1H); 2.69 (m, 4H), 2.51 (dd, 1H); 1.68 (m, 4H); 0.8 (s, 9H); 0.0 (d, 6H).

Intermediate 11

(±)-2-(3-{[tert-butyl(dimethyl)silyl]oxy}-2-hydroxypropyl)-5,6,7,8-tetrahydronaphthalen-1-ol Treatment of (±)-1-[1-(benzyloxy)-5,6,7,8-tetrahydronaphthalen-2-yl]-3-{[tert-butyl(dimethyl)silyl]oxy}propan-2-ol (7.93 g, 0.019 mol) with palladium on carbon (10 wt. %, 0.80 g) generally according to the procedure described for Intermediate 4 gave 5.75 g (92%) of (±)-2-(3-{[tert-butyl(dimethyl)silyl]oxy}-2-hydroxypropyl)-5,6,7,8-tetrahydronaphthalen-1-ol as a colorless oil. $R_f$=0.55 (silica, ethyl acetate:hexanes 1:3); Anal. calcd. for $C_{19}H_{32}O_3Si.0.3C_4H_8O_2$: C, 66.84; H, 9.55. Found: C, 66.47; H, 9.74.

Intermediate 12

(±)-tert-butyl(2,3,6,7,8,9-hexahydronaphtho[1,2-b]furan-2-ylmethoxy)dimethylsilane Treatment of (±)-2-(3-{[tert-butyl(dimethyl)silyl]oxy}-2-hydroxypropyl)-5,6,7,8-tetrahydronaphthalen-1-ol (5.75 g, 0.017 mol) with triphenylphosphine (4.71 g, 0.018 mol) and diethylazodicarboxylate (3.12 g, 0.018 mol) generally according to the procedure described for Intermediate 5 provided 4.38 g (80%) of (±)-tert-butyl(2,3,6,7,8,9-hexahydronaphtho[1,2-b]furan-2-ylmethoxy)dimethylsilane as a colorless oil. $R_f$=0.71 (silica, ethyl acetate:hexanes 1:5); Anal. calcd. for $C_{19}H_{30}O_2Si$: C, 71.64; H, 9.49. Found: C, 71.4; H, 9.62.

Intermediate 13

(±)-2,3,6,7,8,9-hexahydronaphtho[1,2-b]furan-2-ylmethanol

Treatment of (±)-tert-butyl(2,3,6,7,8,9-hexahydronaphtho[1,2-b]furan-2-ylmethoxy)dimethylsilane (4.38 g; 0.014 mol) with tetrabutylammonium fluoride (16.5 mL, 1.0 M solution in tetrahydrofuran) generally according to the procedure described for Intermediate 6 afforded 1.9 g (67%) of (±)-2,3,6,7,8,9-hexahydronaphtho[1,2-b]furan-2-ylmethanol as a colorless oil. $R_f$=0.12 (silica, ethyl acetate:hexanes 1:4); Anal. calcd. for $C_{13}H_{16}O_2.0.1H_2O$: C, 75.77; H, 7.92. Found: C, 75.77; H, 7.93.

Intermediate 14

(±)-2,3,6,7,8,9-hexahydronaphtho[1,2-b]furan-2-ylmethyl 4-methylbenzenesulfonate To a solution of (±)-2,3,6,7,8,9-hexahydronaphtho[1,2-b]furan-2-ylmethanol (1.37 g, 6.71 mmol) in dichloromethane (50 mL) was added p-toluenesulfonyl chloride (2.56 g, 13.41 mmol), 4-(dimethylamino)pyridine (0.164 g, 1.34 mmol), and triethylamine (1.70 g, 16.77 mmol) and the reaction mixture was allowed to stir at 40° C. for 12 h. The reaction mixture was diluted with water (250 mL) and the aqueous layer extracted with dichloromethane (2×150 mL). The combined organic extracts were washed with saturated aqueous sodium chloride, dried (magnesium sulfate), and the solvent was removed in vacuo to provide a crude oil. Purification by flash column chromatography (silica, ethyl acetate:hexanes 1:5) gave 2.05 g (85%) of (±)-2,3,6,7,8,9-hexahydronaphtho[1,2-b]furan-2-ylmethyl 4-methylbenzenesulfonate as a colorless oil. $R_f$=0.5 (silica, ethyl acetate:hexanes 1:4); Anal. calcd. for $C_{20}H_{22}O_4S$: C, 67.01; H, 6.19. Found: C, 66.50; H, 6.27.

Intermediate 15

(±)-benzyl 2,3,6,7,8,9-hexahydronaphtho[1,2-b]furan-2-ylmethylcarbamate

Treatment of (±)-1-(2,3,6,7,8,9-hexahydronaphtho[1,2-b]furan-2-yl)methanamine (0.846 g, 4.16 mmol) with diisopropylethylamine (0.592 g, 4.58 mmol) followed by benzyl chloroformate (0.745 g, 4.37 mmol) generally according to the procedure described for Intermediate 7 provided 1.11 g (79%) of (±)-benzyl 2,3,6,7,8,9-hexahydronaphtho[1,2-b]furan-2-ylmethylcarbamate as a white solid. $R_f$=0.39 (silica, ethyl acetate:hexanes 1:4); mp 88-90° C.; $^1$H NMR (DMSO-$d_6$) $\delta_H$ 7.49 (t, 1H); 7.33 (m, 4H); 6.87 (d, 1H); 6.50 (d, 1H); 5.02 (s, 2H); 4.76 (m, 1H); 3.20 (m, 3H); 2.83 (dd, 1H); 2.62 (s, 2H); 2.49 (m, 2H); 1.67 (m, 4H). Chiral HPLC separation of (±)-benzyl 2,3,6,7,8,9-hexahydronaphtho[1,2-b]furan-2-ylmethylcarbamate (Chiralcel OJ, isopropanol:hexane 9:1) provided two fractions. Fraction 1 ($R_t$=11.576 min, Chiralcel OD, isopropanol:hexanes 1:9); Fraction 2 ($R_t$=14.729 min, Chiralcel OD, isopropanol:hexanes 1:9).

Intermediate 16

5-allyl-4-(benzyloxy)-7-methylindane

Treatment of 7-methylindan-4-ol (10.00 g, 0.067 mol) with potassium carbonate (37.3 g, 0.270 mol) and allyl bromide (9.80 g, 0.081 mol) generally according to the procedure described for Intermediate 1 afforded 4-(allyloxy)-7-methylindane. Refluxing the allyl ether in mesitylene generally according to the procedure described for Intermediate 1 gave 5-allyl-7-methylindan-4-ol. Treatment of the phenyl with potassium carbonate (27.99 g, 0.203 mol) and benzyl bromide (12.70 g, 0.074 mol) generally according to the procedure described for Intermediate 1 provided 8.41 g (45%) of 5-allyl-4-(benzyloxy)-7-methylindane as a colorless oil. $R_f$=0.42 (silica, ethyl acetate:hexanes 1:19); Anal. calcd. for $C_{20}H_{22}O.0.3H_2O$: C, 84.65; H, 8.03. Found: C, 84.64; H, 7.78.

Intermediate 17

(±)-3-[4-(benzyloxy)-7-methyl-2,3-dihydro-1H-inden-5-yl]propane-1,2-diol

Treatment of 5-allyl-4-(benzyloxy)-7-methylindane (8.41 g, 0.030 mol) with AD-mix-α (42.29 g) generally according to the procedure described for Intermediate 2 afforded 9.12 g (97%, 26% ee) of (±)-3-[4-(benzyloxy)-7-methyl-2,3-dihydro-1H-inden-5-yl]propane-1,2-diol as a white solid. $R_f$=0.45 (silica, ethyl acetate:hexanes 1:1); mp 77-80° C.; Anal. calcd. for $C_{20}H_{24}O_3$: C, 76.89; H, 7.74. Found: C, 76.79; H, 7.7.

Intermediate 18

(±)-(5-methyl-3,6,7,8-tetrahydro-2H-indeno[4,5-b]furan-2-yl)methyl 4-methylbenzenesulfonate To a solution of (±)-3-[4-(benzyloxy)-7-methyl-2,3-dihydro-1H-inden-5-yl]propane-1,2-diol (9.12 g, 0.029 mol) in anhydrous pyridine (290 mL) cooled to 0° C. was added p-toluenesulfonyl chloride (5.84 g, 0.031 mol) and the reaction mixture was allowed to stir for at 0° C. 12 h. The reaction mixture was quenched by the addition of water (10 mL) and the reaction mixture was allowed to stir at room temperature for 15 min. The reaction mixture was diluted with ethyl acetate (800 mL) and washed with aqueous hydrogen chloride (4×1000 mL, 2.0 N), water (500 mL), saturated aqueous sodium chloride (500 mL), dried (magnesium sulfate), and the solvent was removed in vacuo to afford (±)-3-[4-(benzyloxy)-7-methyl-2,3-dihydro-1H-inden-5-yl]-2-hydroxypropyl 4-methylbenzenesulfonate as a crude solid. Treatment of the tosylate with palladium on carbon (10 wt. %, 1.50 g) generally according to the procedure described for Intermediate 11 provided (±)-2-hydroxy-3-(4-hydroxy-7-methyl-2,3-dihydro-1H-inden-5-yl)propyl 4-methylbenzenesulfonate. Treatment of the phenyl with triphenylphoshine (10.17 g, 0.039 mol) and diethylazodicarboxylate (6.75 g, 0.039 mol) generally according to the procedure described for Intermediate 12 gave 9.44 g (91%) of (±)-(5-methyl-3,6,7,8-tetrahydro-2H-indeno[4,5-b]furan-2-yl)methyl 4-methylbenzenesulfonate as a white solid. $R_f$=0.62 (silica, ethyl acetate: hexanes 1:4); mp 61-64° C.; Anal. calcd. for $C_{20}H_{22}O_4S$: C, 67.01; H, 6.19. Found: C, 67.02; H, 6.15.

Intermediate 19

(±)-benzyl (5-methyl-3,6,7,8-tetrahydro-2H-indeno[4,5-b]furan-2-yl)methylcarbamate Treatment of (±)-1-(5-methyl-3,6,7,8-tetrahydro-2H-indeno[4,5-b]furan-2-yl)methanamine (2.28 g, 11.2 mmol) with diisopropylethylamine (2.16 g, 16.7 mmol) followed by benzyl chloroformate (2.19 g, 12.8 mmol) generally according to the procedure described for Intermediate 15 gave 4.05 g (81%) of (±)-benzyl (5-methyl-3,6,7,8-tetrahydro-2H-indeno[4,5-b]furan-2-yl)methylcarbamate as a white solid. $R_f$=0.33 (silica, ethyl acetate:hexanes 1:4); mp 109-113° C.; Anal. calcd. for $C_{21}H_{23}NO_3$: C, 74.75; H, 6.87; N, 4.15. Found: C, 74.42; H, 6.91; N, 4.10. Chiral HPLC separation of (±)-benzyl (5-methyl-3,6,7,8-tetrahydro-2H-indeno[4,5-b]furan-2-yl)methylcarbamate (Chiralcel OJ, methanol) provided two fractions. Fraction 1 ($R_t$=19.001 min, Chiralcel OJ, methanol); Fraction 2 ($R_t$=23.125 min, Chiralcel OJ, methanol).

Intermediate 20

(+)-benzyl (5-methyl-3,6,7,8-tetrahydro-2H-indeno[4,5-b]furan-2-yl)methylcarbamate Isolation of fraction 1 obtained from the chiral HPLC separation (Chiralcel OJ, methanol) of (±)-benzyl (5-methyl-3,6,7,8-tetrahydro-2H-indeno[4,5-b]furan-2-yl)methylcarbamate provided (+)-benzyl (5-methyl-3,6,7,8-tetrahydro-2H-indeno[4,5-b]furan-2-yl)methylcarbamate as a white solid. $[\alpha]_D^{25}$=+36.02 (c 10.0 in chloroform); mp 128-131° C.; Anal. calcd. for $C_{21}H_{23}NO_3.0.2H_2O$: C, 73.96; H, 6.92; N, 4.11. Found: C, 73.86; H, 6.73; N, 4.07.

Intermediate 21

(−)-benzyl (5-methyl-3,6,7,8-tetrahydro-2H-indeno[4,5-b]furan-2-yl)methylcarbamate Isolation of fraction 2 obtained from the chiral HPLC separation (Chiralcel OJ, methanol) of (±)-benzyl (5-methyl-3,6,7,8-tetrahydro-2H-indeno[4,5-b]furan-2-yl)methylcarbamate provided (−)-benzyl (5-methyl-3,6,7,8-tetrahydro-2H-indeno[4,5-b]furan-2-yl)methylcarbamate as a white solid. $[\alpha]_D^{25}$=−37.00 (c 10.0 in chloroform); mp 128-131° C.; Anal. calcd. for $C_{21}H_{23}NO_3.0.2H_2O$: C, 73.96; H, 6.92; N, 4.11. Found: C, 73.77; H, 6.77; N, 4.05.

Intermediate 22

(±)-1-[1-(benzyloxy)-2-naphthyl]-3-{[tert-butyl(dimethyl)silyl]oxy}propan-2-ol

Treatment of 2-allyl-1-(benzyloxy)naphthalene (15.00 g, 54.7 mmol) with AD-mix-α (76.54 g) generally according to the procedure described for Intermediate 2 afforded 16.00 g (69%) of (±)-3-[1-(benzyloxy)-2-naphthyl]propane-1,2-diol as an oil. Treatment of the diol with tert-butyldimethylsilyl chloride (8.60 g, 57.1 mmol) and imidazole (4.42 g, 64.9 mmol) generally according to the procedure described for Intermediate 3 gave 19.3 g (83%, 42% ee) of (±)-1-[1-(benzyloxy)-2-naphthyl]-3-{[tert-butyl(dimethyl)silyl]oxy}propan-2-ol as a colorless oil. Anal. calcd. for $C_{26}H_{34}O_3Si.0.5H_2O$: C, 72.35; H, 8.17. Found: C, 72.34; H, 8.16.

Intermediate 23

(±)-tert-butyl(2,3-dihydronaphtho[1,2-b]furan-2-ylmethoxy)dimethylsilane

Treatment of (γ)-1-[1-(benzyloxy)-2-naphthyl]-3-{[tert-butyl(dimethyl)silyl]oxy}propan-2-ol (19.00 g, 45.0 mmol) with palladium on carbon (10 wt. %, 1.90 g) generally according to the procedure described for Intermediate 4 provided 13.2 g (91%) of (±)-2-(3-{[tert-butyl(dimethyl)silyl]oxy}-2-hydroxypropyl)-1-naphthol as an oil. Treatment of the phenyl with triphenylphosphine (10.52 g, 40.1 mmol) followed by diethylazodicarboxylate (6.98 g, 40.1 mmol) generally according to the procedure described for Intermediate 4 afforded 5.49 g (44%) of (±)-tert-butyl(2,3-dihydronaphtho[1,2-b]furan-2-ylmethoxy)dimethylsilane as a colorless oil. Anal. calcd. for $C_{19}H_{26}O_2Si$: C, 72.56; H, 8.33. Found: C, 72.23; H, 8.61.

Intermediate 24

(±)-2-(azidomethyl)-2,3-dihydronaphtho[1,2-b]furan

Treatment of (±)-tert-butyl(2,3-dihydronaphtho[1,2-b]furan-2-ylmethoxy)dimethylsilane (2.70 g; 8.59 mmol) with tetrabutylammonium fluoride (9.4 mL, 1.0 M solution in tetrahydrofuran) generally according to the procedure described for Intermediate 6 gave (±)-2,3-dihydronaphtho[1,2-b]furan-2-ylmethanol. Treatment of the alcohol with p-toluenesulfonyl chloride (1.64 g, 8.59 mmol), 4-(dimethylamino)pyridine (0.105 g, 0.86 mmol), and triethylamine (1.67 g, 12.89 mmol) generally according to the procedure described for Intermediate 14 provided (±)-2,3-dihydronaphtho[1,2-b]furan-2-ylmethyl 4-methylbenzenesulfonate. To a solution of the tosylate in dimethylsulfoxide (50 mL) was added sodium azide (0.558 g, 8.59 mmol) and the reaction mixture was allowed to stir at 70° C. for 12 h, cooled to room temperature, diluted with water (200 mL) and extracted with diethyl ether (2×100 mL). The combined organic extracts were washed with water (4×75 mL), saturated aqueous sodium chloride (75 mL), dried (magnesium sulfate), and the solvent was removed in vacuo to provide a crude oil. Purification by flash column chromatography (silica, ethyl acetate:hexanes 1:9) provided 1.38 g (71%) of (±)-2-(azidomethyl)-2,3-dihydronaphtho[1,2-b]furan as a colorless oil. $R_f$=0.46 (silica, ethyl acetate: hexanes 1:9); Anal. calcd. for $C_{13}H_{11}N_3O.0.1H_2O$: C, 68.77; H, 4.97; N, 18.51. Found: C, 68.4; H, 4.62; N, 18.12.

Intermediate 25

(±)-benzyl 2,3-dihydronaphtho[1,2-b]furan-2-ylmethylcarbamate

Treatment of (±)-1-(2,3-dihydronaphtho[1,2-b]furan-2-yl)methanamine (1.19 g, 5.97 mmol) with diisopropylethylamine (0.849 g, 6.57 mmol) followed by benzyl chloroformate (1.07 g, 6.27 mmol) generally according to the procedure described for Intermediate 7 afforded 1.80 g (90%) of (±)-benzyl 2,3-dihydronaphtho[1,2-b]furan-2-ylmethylcarbamate as a white solid. $R_f$=0.47 (silica, ethyl acetate: hexanes 1:4); mp 110-112° C.; Anal. calcd. for $C_{21}H_{19}NO_3$: C, 75.66; H, 5.74; N, 4.2. Found: C, 75.4; H, 5.57; N, 4.12. Chiral HPLC separation of (±)-benzyl 2,3-dihydronaphtho[1,2-b]furan-2-ylmethylcarbamate (Chiralcel OJ, ethanol) provided two fractions. Fraction 1 ($R_t$=19.572 min, Chiralcel OJ, ethanol); Fraction 2 ($R_t$=30.782 min, Chiralcel OJ, ethanol).

Intermediate 26

(±)-benzyl 2,3,5,6,7,8-hexahydronaphtho[2,3-b]furan-2-ylmethylcarbamate

Treatment of a mixture of 1-allyl-5,6,7,8-tetrahydronaphthalen-2-yl benzyl ether and 3-allyl-5,6,7,8-tetrahydronaphthalen-2-yl benzyl ether (26.12 g, 0.094 mol) with AD-mix-α (131.36 g) generally according to the procedure described for Intermediate 2 provided a mixture of (±)-3-[3-(benzyloxy)-5,6,7,8-tetrahydronaphthalen-2-yl]propane-1,2-diol and (±)-3-[2-(benzyloxy)-5,6,7,8-tetrahydronaphthalen-1-yl]propane-1,2-diol. Treatment of the diol (5.00 g, 16.00 mmol) with tert-butyldimethylsilyl chloride (2.65 g, 17.6 mmol) and imidazole (1.31 g, 19.2 mmol) generally according to the procedure described for Intermediate 3 afforded (±)-1-[3-(benzyloxy)-5,6,7,8-tetrahydronaphthalen-2-yl]-3-{[tert-butyl(dimethyl)silyl]oxy}propan-2-ol and (±)-1-[2-(benzyloxy)-5,6,7,8-tetrahydronaphthalen-1-yl]-3-{[tert-butyl(dimethyl)silyl]oxy}propan-2-ol. Treatment of the benzyl ether (5.2 g, 12.2 mmol) with palladium on carbon (10 wt. %, 0.52 g) generally according to the procedure described for Intermediate 4 gave (±)-3-(3-{[tert-butyl(dimethyl)silyl]oxy}-2-hydroxypropyl)-5,6,7,8-tetrahydronaphthalen-2-ol and (±)-1-(3-{[tert-butyl(dimethyl)silyl]oxy}-2-hydroxypropyl)-5,6,7,8-tetrahydronaphthalen-2-ol. Treatment of the phenyl (4.32 g, 12.8 mmol) with triphenylphosphine (4.04 g, 15.4 mmol) and diethylazodicarboxylate (2.68 g, 15.4 mmol) generally according to the procedure described for Intermediate 5 provided (±)-tert-butyl(2,3,5,6,7,8-hexahydronaphtho[2,3-b]furan-2-ylmethoxy)dimethylsilane and (±)-tert-butyl(1,2,6,7,8,9-hexahydronaphtho[2,1-b]furan-2-ylmethoxy)dimethylsilane. Treatment of the dihydrobenzofuran (2.82 g, 8.91 mmol) with tetrabutylammonium fluoride (10.0 mL, 1.0 M solution in tetrahydrofuran) generally according to the procedure described for Intermediate 6 afforded (±)-2,3,5,6,7,8-hexahydronaphtho[2,3-b]furan-2-ylmethanol and (±)-1,2,6,7,8,9-hexahydronaphtho[2,1-b]furan-2-ylmethanol. Treatment of the alcohol (2.53 g, 12.4 mmol) with p-toluenesulfonyl chloride (3.54 g, 18.6 mmol), 4-(dimethylamino)pyridine (0.151 g, 1.24 mmol), and triethylamine (2.26 g, 22.3 mmol) generally according to the procedure described for Intermediate 14 provided (±)-2,3,5,6,7,8-hexahydronaphtho[2,3-b]furan-2-ylmethyl 4-methylbenzenesulfonate and (±)-1,2,6,7,8,9-hexahydronaphtho[2,1-b]furan-2-ylmethyl 4-methylbenzenesulfonate. Treatment of the tosylate (3.00 g, 8.37 mmol) with sodium azide (1.63 g, 25.1 mmol) generally according to the procedure described for Intermediate 24 afforded (±)-2-(azidomethyl)-2,3,5,6,7,8-hexahydronaphtho[2,3-b]furan and (±)-2-(azidomethyl)-1,2,6,7,8,9-hexahydronaphtho[2,1-b]furan. Treatment of the resulting azide with palladium on carbon (10 wt. %, 0.191 g) generally according to the procedure described for Example 2 afforded (±)-1-(2,3,5,6,7,8-hexahydronaphtho[2,3-b]furan-2-yl)methanamine and (±)-1-(1,2,6,7,8,9-hexahydronaphtho[2,1-b]furan-2-yl)methanamine. Treatment of the amine (1.34 g, 6.57 mmol) with diisopropylethylamine (2.12 g, 16.44 mmol) and benzyl chloroformate (1.23 g, 7.23 mmol) generally according to the procedure described for Intermediate 7 gave (±)-benzyl 2,3,5,6,7,8-hexahydronaphtho[2,3-b]furan-2-ylmethylcarbamate and (±)-benzyl 1,2,6,7,8,9-hexahydronaphtho[2,1-b]furan-2-ylmethylcarbamate.

Chiral HPLC separation of the consititutional isomers (Chiralcel OJ, ethanol) provided benzyl 2,3,5,6,7,8-hexahydronaphtho[2,3-b]furan-2-ylmethylcarbamate as a white solid. mp 114-115° C.; Anal. calcd. for $C_{21}H_{23}NO_3$: C, 74.75; H, 6.87; N, 4.15. Found: C, 74.7; H, 6.95; N, 4.12.

Intermediate 27

(1R*,4S*)-5-(allyloxy)-8-methoxy-1,2,3,4-tetrahydro-1,4-methanonaphthalene

Treatment of (1R*,4S*)-8-methoxy-1,2,3,4-tetrahydro-1,4-methanonaphthalen-5-ol (14.61 g, 0.077 mol) with potassium carbonate (31.84 g, 0.23 mol) and allyl bromide (10.68 g, 0.088 mol) generally according to the procedure described for Intermediate 1 provided 15.8 g (89%) of (1R*,4S*)-5-(allyloxy)-8-methoxy-1,2,3,4-tetrahydro-1,4-methanonaphthalene as a colorless oil. Anal. calcd. for $C_{15}H_{18}O_2 \cdot 0.3H_2O$: C, 76.44; H, 7.95. Found: C, 76.43; H, 7.79.

Intermediate 28

(1R*,4S*)-6-allyl-8-methoxy-1,2,3,4-tetrahydro-1,4-methanonaphthalen-5-ol

Treatment of (1R*,4S*)-5-(allyloxy)-8-methoxy-1,2,3,4-tetrahydro-1,4-methanonaphthalene (15.8 g, 0.069 mol) in refluxing mesitylene generally according to the procedure described for Intermediate 1 gave 12.58 g (80%) of (1R*,4S*)-6-allyl-8-methoxy-1,2,3,4-tetrahydro-1,4-methanonaphthalen-5-ol as a colorless oil. Anal. calcd. for $C_{20}H_{22}O \cdot 0.2H_2O$: C, 77.02; H, 7.93. Found: C, 76.68; H, 7.88.

Intermediate 29

(1R*,4S*)-6-allyl-5-(benzyloxy)-8-methoxy-1,2,3,4-tetrahydro-1,4-methanonaphthalene Treatment of (1R*,4S*)-6-allyl-8-methoxy-1,2,3,4-tetrahydro-1,4-methanonaphthalen-5-ol (14.2 g, 61.66 mmol) with potassium carbonate (34.09 g, 0.247 mol), benzyl bromide (11.07 g, 64.74 mmol), and tetrabutylammonium iodide (0.224 g, 6.166 mmol) generally according to the procedure described for Intermediate 1 provided 17.86 g (90%) of (1R*,4S*)-6-allyl-5-(benzyloxy)-8-methoxy-1,2,3,4-tetrahydro-1,4-methanonaphthalene as a colorless oil. Anal. calcd. for $C_{22}H_{24}O_2 \cdot 0.5H_2O$: C, 80.21; H, 7.65. Found: C, 79.81; H, 7.48.

Intermediate 30

(2S*)-3-[(1R*,4S*)-5-(benzyloxy)-8-methoxy-1,2,3,4-tetrahydro-1,4-methanonaphthalen-6-yl]propane-1,2-diol Treatment of (1R*,4S*)-6-allyl-5-(benzyloxy)-8-methoxy-1,2,3,4-tetrahydro-1,4-methanonaphthalene (17.80 g, 55.55 mmol) with AD-mix-α (77.77 g) generally according to the procedure described for Intermediate 2 provided 13.99 g (71%) of (2S*)-3-[(1R*,4S*)-5-(benzyloxy)-8-methoxy-1,2,3,4-tetrahydro-1,4-methanonaphthalen-6-yl]propane-1,2-diol as a colorless oil. Anal. calcd. for $C_{22}H_{26}O_4 \cdot 0.3H_2O$: C, 73.43; H, 7.45. Found: C, 73.23; H, 7.7.

Intermediate 31

[(2R*,6R*,9S*)-5-methoxy-2,3,6,7,8,9-hexahydro-6,9-methanonaphtho[1,2-b]furan-2-yl]methyl 4-methylbenzenesulfonate Treatment of (2S*)-3-[(1R*,4S*)-5-(benzyloxy)-8-methoxy-1,2,3,4-tetrahydro-1,4-methanonaphthalen-6-yl]propane-1,2-diol (13.95 g, 39.56 mmol) with p-toluenesulfonyl chloride (8.25 g, 43.92 mmol) in anhydrous pyridine (350 mL) generally according to the procedure described for Intermediate 18 gave (2S*)-3-[(1R*,4S*)-5-(benzyloxy)-8-methoxy-1,2,3,4-tetrahydro-1,4-methanonaphthalen-6-yl]-2-hydroxypropyl 4-methylbenzenesulfonate. Treatment of the tosylate with palladium on carbon (10 wt. %, 1.6 g) generally according to the procedure described for Intermediate 4 provided 12.77 g (77%) of (2S*)-2-hydroxy-3-[(1R*,4S*)-5-hydroxy-8-methoxy-1,2,3,4-tetrahydro-1,4-methanonaphthalen-6-yl]propyl 4-methylbenzenesulfonate. Treatment of the phenyl (12.73 g, 30.4 mmol) with triphenylphosphine (8.78 g, 33.5 mmol) followed by diethylazodicarboxylate (5.83 g, 33.5 mmol) generally according to the procedure described for Intermediate 5 afforded 7.67 g (48%) of [(2R*,6R*,9S*)-5-methoxy-2,3,6,7,8,9-hexahydro-6,9-methanonaphtho[1,2-b]furan-2-yl]methyl 4-methylbenzenesulfonate as a colorless oil. Anal. calcd. for $C_{22}H_{24}O_5S$: C, 65.98; H, 6.04. Found: C, 65.61; H, 5.92.

Intermediate 32

6-allyl-5-(benzyloxy)-8-methoxy-1,2,3,4-tetrahydro-1,4-ethanonaphthalene

Treatment of 8-methoxy-1,2,3,4-tetrahydro-1,4-ethanonaphthalen-5-ol (11.30 g, 0.055 mol) with potassium carbonate (22.94 g, 0.166 mol) and allyl bromide (7.36 g, 0.061 mol) generally according to the procedure described for Intermediate 1 afforded 5-(allyloxy)-8-methoxy-1,2,3,4-tetrahydro-1,4-ethanonaphthalene. Treatment of the allyl ether in refluxing mesitylene generally according to the procedure described for Intermediate 1 gave 6-allyl-8-methoxy-1,2,3,4-tetrahydro-1,4-ethanonaphthalen-5-ol. Treatment of the phenyl with potassium carbonate (20.04 g, 0.145 mol), benzyl bromide (9.09 g, 0.053 mol), and tetrabutylammonium iodide (1.79 g, 0.005 mol) generally according to the procedure described for Intermediate 1 provided 15.05 g (82%) of 6-allyl-5-(benzyloxy)-8-methoxy-1,2,3,4-tetrahydro-1,4-ethanonaphthalene as a colorless oil. Anal. calcd. for $C_{23}H_{26}O_2 \cdot 0.1H_2O$: C, 82.16; H, 7.85. Found: C, 81.98; H, 7.71.

Intermediate 33

(±)-3-[5-(benzyloxy)-8-methoxy-1,2,3,4-tetrahydro-1,4-ethanonaphthalen-6-yl]propane-1,2-diol Treatment of 6-allyl-5-(benzyloxy)-8-methoxy-1,2,3,4-tetrahydro-1,4-ethanonaphthalene (15.00 g, 44.8 mmol) with AD-mix-α (62.79 g) generally according to the procedure described for Intermediate 2 provided 15.85 g (96%, 36% ee) of (±)-3-[5-(benzyloxy)-8-methoxy-1,2,3,4-tetrahydro-1,4-ethanonaphthalen-6-yl]propane-1,2-diol as a colorless oil. Anal. calcd. for $C_{23}H_{28}O_4 \cdot 0.4H_2O$: C, 73.53; H, 7.73. Found: C, 73.14; H, 7.59.

Intermediate 34

(±)-3-[5-(benzyloxy)-8-methoxy-1,2,3,4-tetrahydro-1,4-ethanonaphthalen-6-yl]-2-hydroxypropyl 4-methylbenzenesulfonate Treatment of (±)-3-[5-(benzyloxy)-8-methoxy-1,2,3,4-tetrahydro-1,4-ethanonaphthalen-6-yl]propane-1,2-diol (15.82 g, 0.043 mol) with p-toluenesulfonyl chloride (9.00 g, 0.047 mol) in anhydrous pyridine (400 mL) generally according to the procedure described for Intermediate 18 gave 20.12 g (90%) of (±)-3-[5-(benzyloxy)-8-methoxy-1,2,3,4-tetrahydro-1,4-ethanonaphthalen-6-yl]-2-hydroxypropyl 4-methyl-

Intermediate 35

(±)-2-hydroxy-3-(5-hydroxy-8-methoxy-1,2,3,4-tetrahydro-1,4-ethanonaphthalen-6-yl)propyl 4-methylbenzenesulfonate Treatment of (±)-3-[5-(benzyloxy)-8-methoxy-1,2,3,4-tetrahydro-1,4-ethanonaphthalen-6-yl]-2-hydroxypropyl 4-methylbenzenesulfonate (20.00 g, 38.3 mmol) with palladium on carbon (10 wt. %, 2.0 g) generally according to the procedure described for Intermediate 4 provided 15.18 g (92%) of (±)-2-hydroxy-3-(5-hydroxy-8-methoxy-1,2,3,4-tetrahydro-1,4-ethanonaphthalen-6-yl)propyl 4-methylbenzenesulfonate as a brown oil. Anal. calcd. for $C_{23}H_{28}O_6S$: C, 63.34; H, 6.56. Found: C, 62.98; H, 6.66.

Intermediate 36

(±)-(5-methoxy-2,3,6,7,8,9-hexahydro-6,9-ethanonaphtho[1,2-b]furan-2-yl)methyl 4-methylbenzenesulfonate Treatment of (±)-2-hydroxy-3-(5-hydroxy-8-methoxy-1,2,3,4-tetrahydro-1,4-ethanonaphthalen-6-yl)propyl 4-methylbenzenesulfonate (15.14 g, 35.0 mmol) with triphenylphosphine (10.10 g, 38.5 mmol) followed by diethylazodicarboxylate (6.71 g, 38.5 mmol) generally according to the procedure described for Intermediate 5 afforded 10.9 g (75%) of (±)-(5-methoxy-2,3,6,7,8,9-hexahydro-6,9-ethanonaphtho[1,2-b]furan-2-yl)methyl 4-methylbenzenesulfonate as a white solid. mp 136-141° C.; Anal. calcd. for $C_{23}H_{26}O_5S$: C, 66.64; H, 6.32. Found: C, 66.53; H, 6.51.

Intermediate 37

2-allyl-4-chloro-1-naphthol

To a solution of 4-chloro-1-naphthanol (17.8 g, 0.10 mol) in N,N-dimethylformamide (600 mL) was added sodium hydride (4.4 g, 0.11 mol) and the mixture was stirred for 30 min. Allyl bromide (14.5 g, 0.12 mol) was added and the reaction mixture was allowed to stir at room temperature for 20 h. The solvent was removed in vacuo and the residue was diluted with ethyl acetate (500 mL), washed with water (2×250 mL), saturated aqueous sodium chloride (250 mL), dried (sodium sulfate) and concentrated to a brown oil. The oil was re-dissolved in mesitylene (1000 mL) and heated at reflux for 24 h. The reaction mixture was allowed to cool to room temperature and the solvent was removed in vacuo to provide a crude oil. Purification by flash chromatography (silica, hexanes) afforded 20.0 g (91%) of 2-allyl-4-chloro-1-naphthol as a white solid. mp 55-57° C.; Anal. calcd. for $C_{13}H_{11}ClO$: C, 71.40; H, 5.07. Found: C, 71.26; H, 5.15.

Intermediate 38

(±)-3-[1-(benzyloxy)-4-chloro-2-naphthyl]propane-1,2-diol

To a solution of 2-allyl-4-chloro-1-naphthol (20.0 g, 0.091 mol) in N,N-dimethylformamide (700 mL) was added sodium hydride (60 wt. %, 4.39 g, 0.11 mol) and the reaction mixture was allowed to stir at room temperature for 30 min. Benzyl bromide (18.8 g, 0.11 mol) was then added and the reaction mixture was allowed to stir at room temperature for 2 h. The solvent was removed in vacuo to provide a crude oil. The residue was re-dissolved in ethyl acetate (500 mL) and the organic layer was washed with water (2×250 mL), saturated aqueous sodium chloride (250 mL), dried (sodium sulfate) and the solvent was removed in vacuo to provide a crude oil. Purification by flash column chromatography (silica, dichloromethane:hexanes 1:4) provided 23.0 g (82%) of 2-allyl-1-(benzyloxy)-4-chloronaphthalene as a light brown oil. Treatment of the benzyl ether with AD-mix-α (104.3 g) generally according to the procedure described for Intermediate 2 afforded 24.0 g (94%) of (±)-3-[1-(benzyloxy)-4-chloro-2-naphthyl]propane-1,2-diol as a white solid. mp 69-71° C.; Anal. calcd. for $C_{20}H_{19}ClO$: C, 70.07; H, 5.59. Found: C, 68.01; H, 5.47.

Intermediate 39

(±)-3-[1-(benzyloxy)-4-chloro-2-naphthyl]-2-hydroxypropyl 4-methylbenzenesulfonate Treatment of (±)-3-[1-(benzyloxy)-4-chloro-2-naphthyl]propane-1,2-diol (24 g, 0.07 mol) with p-toluenesulfonyl chloride (14 g, 0.074 mol) in pyridine (600 mL) generally according to the procedure described for Intermediate 18 gave 27.9 g (80%) of (±)-3-[1-(benzyloxy)-4-chloro-2-naphthyl]-2-hydroxypropyl 4-methylbenzenesulfonate as a white solid. mp 85-87° C.; Anal. calcd. for $C_{27}H_{25}ClO_5S$: C, 65.25; H, 5.07. Found: C, 65.37; H, 4.97.

Intermediate 40

(±)-benzyl (5-chloro-2,3-dihydronaphtho[1,2-b]furan-2-yl)methylcarbamate

Treatment of (±)-1-(5-chloro-2,3-dihydronaphtho[1,2-b]furan-2-yl)methanamine (0.83 g, 3.07 mmol) with diisopropylethylamine (1.20 g, 9.28 mmol) followed by benzyl chloroformate (0.79 g, 4.60 mmol) generally according to the procedure described for Intermediate 7 provided 1.00 g (89%) of (±)-benzyl (5-chloro-2,3-dihydronaphtho[1,2-b]furan-2-yl)methylcarbamate as a white solid. mp 117-119° C.; Anal. calcd. for $C_{21}H_{18}ClNO_3.0.5H_2O$: C, 66.93; H, 5.08; N, 3.72. Found: C, 66.81; H, 4.96; N, 3.67.

Intermediate 41

(±)-methyl (5-chloro-2,3-dihydronaphtho[1,2-b]furan-2-yl)methylcarbamate

Treatment of (±)-(5-chloro-2,3-dihydronaphtho[1,2-b]furan-2-yl)methylamine (2.60 g, 9.62 mmol) with diisopropylethylamine (3.73 g, 28.85 mmol) and methyl chloroformate (1.36 g, 9.62 mmol) generally according to the procedure described for Intermediate 7 afforded 2.60 g (93%) of (±)-methyl (5-chloro-2,3-dihydronaphtho[1,2-b]furan-2-yl)methylcarbamate as a white solid. mp 128-130° C.; Anal. calcd. for $C_{15}H_{14}ClNO_3$: C, 61.76; H, 4.84; N, 4.80. Found: C, 61.43; H, 4.87; N, 4.68.

Intermediate 42

-(allyloxy)-4-chloro-2-methoxybenzene

Treatment of 4-chloro-2-methoxyphenyl (40.00 g, 0.25 mol) in N,N-dimethylformamide (600 mL) with sodium hydride (60 wt. %, 12.0 g, 0.30 mol,) followed by allyl bromide (40.54 g, 0.34 mol) generally according to the procedure described for Intermediate 37 afforded 50.0 g (99%) of 1-(allyloxy)-4-chloro-2-methoxybenzene as a light brown oil. $^1$H NMR (CDCl$_3$) $\delta_H$ 6.80 (m, 3H); 6.08 (m, 1H); 5.35 (dd, 2H); 4.60 (dd, 2H); 3.85 (s, 3H).

Intermediate 43

2-allyl-4-chloro-6-methoxyphenyl

Treatment of 1-(allyloxy)-4-chloro-2-methoxybenzene (50 g, 0.25 mol) in refluxing mesitylene (1500 mL) generally according to the procedure described for Intermediate 1 provided 44.7 g (89%) of 2-allyl-4-chloro-6-methoxyphenyl as a pale yellow oil. $^1$H NMR (CDCl$_3$) $\delta_H$ 6.78 (m, 2H); 6.00 (m, 1H); 5.65 (s, 1H); 5.10 (m, 2H); 3.85 (s, 3H); 3.40 (dd, 2H).

Intermediate 44

2-allyl-4-chloro-6-methoxyphenyl trifluoromethanesulfonate

To a solution of 2-allyl-4-chloro-6-methoxyphenyl (24.8 g, 0.125 mol) in dichloromethane (500 mL) cooled to 0° C. was added diisopropylethylamine (28.3 mL 0.162 mol) followed by trifluoromethanesulfonic anhydride (45.8 g, 0.162 mol) and the reaction mixture was allowed to stir at room temperature for 2 h. The reaction mixture was diluted with dichloromethane (500 mL) and the organic layer was washed with aqueous hydrogen chloride (1.0 N, 2×500 mL), saturated aqueous sodium bicarbonate (500 mL), and saturated aqueous sodium chloride (500 mL), dried (sodium sulfate) and the solvent removed in vacuo to provide a crude oil. Purification by flash column chromatography (silica, hexanes) gave 30.0 g (75%) of 2-allyl-4-chloro-6-methoxyphenyl trifluoromethanesulfonate as a pale yellow oil. $^1$H N (CDCl$_3$) $\delta_H$ 6.90 (s, 2H); 5.90 (m, 1H); 5.20 (m, 2H); 3.90(s, 3H); 3.45 (dd, 2H).

Intermediate 45

6-chloro-4-methoxyindane

To 9-borabicyclo[3.3.1]nonane (130 mL, 0.5 M in tetrahydrofuran) cooled to 0° C. was added 2-allyl-4-chloro-6-methoxyphenyl trifluoromethanesulfonate (16.5 g, 0.050 mol) in tetrahydrofuran (100 mL), dichloro[1,1'-bis(diphenylphosphino)ferrocene]palladium(II) dichloromethane adduct (1.5 g, 1.84 mmol), and potassium phosphate (16.0 g, 0.075 mol) and the reaction mixture was heated at reflux for 20 h. The reaction mixture was allowed to cool to room temperature and aqueous sodium hydroxide (2.5 N, 30 mL) was added followed by hydrogen peroxide (30 wt. %, 25 mL) and stirring was continued for 1 h. The solvent was removed in vacuo to provide a crude oil. Purification by flash column chromatography (silica, hexanes) provided 6.2 g (68%) of 6-chloro-4-methoxyindane as a white solid. mp 38-40° C.; Anal. calcd. for C$_{10}$H$_{11}$ClO: C, 65.76; H, 6.07. Found: C, 66.08; H, 6.11.

Intermediate 46

6-chloroindan-4-ol

To 6-chloro-4-methoxyindane (12.0 g, 0.072 mol) was added hydrogen bromide (30 wt. % in acetic acid, 325 mL) and the reaction mixture was stirred at 50° C. for 24 h. The reaction mixture was cooled to room temperature and diluted with ethyl acetate (750 mL), washed with water (3×500 mL), saturated aqueous sodium bicarbonate (2×500 m/L), saturated aqueous sodium chloride (500 mL), dried (sodium sulfate) and the solvent was removed in vacuo to provide a brown oil. Purification by flash column chromatography (silica, dichloromethane) provided 10.5 g (80%) of 6-chloroindan-4-ol as a pale yellow solid. mp 56-59° C.; Anal. calcd. for C$_9$H$_9$ClO.0.2H$_2$O: C, 62.77; H, 5.50. Found: C, 62.75; H, 5.26.

Intermediate 47

4-(allyloxy)-6-chloroindane

Treatment of 6-chloro-4-indanol (6.5 g, 0.0385 mol) with sodium hydride (2.12 g, 0.053 mol) followed by allyl bromide (6.99 g, 0.058 mol) generally according to the procedure described for Intermediate 37 provided 4-(allyloxy)-6-chloroindane a brown oil. $^1$H NMR (CDCl$_3$) $\delta_H$ 6.82 (s, 1H); 6.62 (s, 1H); 6.00 (m, 1H); 5.40 (dd, 1H); 5.30 (dd, 1H); 4.50 (dd, 2H); 2.90 (t, 2H); 2.85 (t, 2H); 2.10(m, 2H).

Intermediate 48

5-allyl-6-chloroindan-4-ol

Treatment of 4-(allyloxy)-6-chloroindane (8.0 g, 0.038 mol) in refluxing mesitylene (270 mL) generally according to the procedure described for Intermediate 1 afforded 4.5 g (56%) of 5-allyl-6-chloroindan-4-ol as a colorless oil which solidified into a white solid upon standing. mp 37-39° C.; Anal. calcd. for C$_{12}$H$_{13}$ClO.0.1H$_2$O: C, 68.48; H, 6.32. Found: C, 68.54; H, 6.29.

Intermediate 49

5-allyl-4-(benzyloxy)-6-chloroindane

Treatment of 5-allyl-6-chloroindan-4-ol (4.5 g, 0.0216 mol) with sodium hydride (60 wt. %, 1.32 g, 0.033 mol) followed by benzyl bromide (6.0 g, 0.035 mol) generally according to the procedure described for Intermediate 38 gave 5.76 g (89%) of 5-allyl-4-(benzyloxy)-6-chloroindane as a colorless oil. $^1$H NMR (CDCl$_3$) $\delta_H$ 7.40 (m, 5H); 7.05 (s, 1H); 6.00 (m, 1H); 5.00(m, 2H); 4.90 (s, 2H); 3.53 (dd, 2H); 2.90 (m, 4H); 2.05 (m, 2H).

Intermediate 50

(±)-3-[4-(benzyloxy)-6-chloro-2,3-dihydro-1H-inden-5-yl]propane-1,2-diol

Treatment of 5-allyl-4-(benzyloxy)-6-chloroindane (5.76 g, 0.0193 mol) with AD-mix-α (27.0 g) generally according to the procedure described for Intermediate 2 gave 5.76 g (91%) of (±)-3-[4-(benzyloxy)-6-chloro-2,3-dihydro-1H-inden-5-yl]propane-1,2-diol as a white solid. mp 101-104° C.; Anal. calcd. for C$_{19}$H$_{21}$O$_3$Cl: C, 68.57; H, 6.36. Found: C, 68.24; H, 6.33.

Intermediate 51

(±)-3-[4-(benzyloxy)-6-chloro-2,3-dihydro-1H-inden-5-yl]-2-hydroxypropyl 4-methylbenzenesulfonate Treatment of (±)-3-[4-(benzyloxy)-6-chloro-2,3-dihydro-1H-inden-5-yl]propane-1,2-diol (5.60 g, 0.0168 mol) with p-toluenesulfonyl chloride (3.70 g, 0.0194 mol) in pyridine (200 mL) generally according to the procedure described for Intermediate 18 provided 6.30 g (77%) of (±)-3-[4-(benzyloxy)-6-chloro-2,3-dihydro-1H-inden-5-yl]-2-hydroxypropyl 4-methylbenzenesulfonate as a light yellow oil. $^1$H NMR (DMSO-d$_6$) $^8$H 7.65(d, 2H); 7.40(m, 7H); 7.05(s, 1H); 5.25(s, 1H); 4.90(s, 2H); 3.80(m, 3H); 2.90(m, 2H); 2.80(m, 3H); 2.65(dd, 1H); 2.40(s, 3H); 2.00(m, 2H).

Intermediate 52

(±)-3-(6-chloro-4-hydroxy-2,3-dihydro-1H-inden-5-yl)-2-hydroxypropyl 4-methylbenzenesulfonate Treatment of (±)-3-[4-(benzyloxy)-6-chloro-2,3-dihydro-1H-inden-5-yl]-2-hydroxypropyl 4-methylbenzenesulfonate (6.30 g, 0.013 mol) with palladium on carbon (5 wt. %, 0.51 g) and hydrogen chloride (3.4 mL, 4 M in isopropanol) generally according to the procedure described for Intermediate 4 afforded 4.7 g (91%) of (±)-3-(6-chloro-4-hydroxy-2,3-dihydro-1H-inden-5-yl)-2-hydroxypropyl 4-methylbenzenesulfonate as a light yellow solid. mp 125-127° C.; Anal. calcd. for C$_{19}$H$_{21}$ClO$_5$S.0.1H$_2$O: C, 57.24; H, 5.36. Found: C, 56.92; H, 5.23.

Intermediate 53

(±)-(4-chloro-3,6,7,8-tetrahydro-2H-indeno[4,5-b]furan-2-yl)methyl 4-methylbenzenesulfonate Treatment of (±)-3-(6-chloro-4-hydroxy-2,3-dihydro-1H-inden-5-yl)-2-hydroxypropyl 4-methylbenzenesulfonate (4.7 g, 0.012 mol) with triphenylphosphine (4.64 g, 0.018 mol) and diisopropylazodicarboxylate (3.57 g, 0.018 mol) generally according to the procedure described for Intermediate 5 gave 4.09 g (91%) of (±)-(4-chloro-3,6,7,8-tetrahydro-2H-indeno[4,5-b]furan-2-yl)methyl 4-methylbenzenesulfonate as a white solid. mp 95-97° C.; Anal. calcd. for C$_{19}$H$_{19}$ClO$_4$S: C, 60.23; H, 5.05. Found: C, 60.12; H, 4.97.

Intermediate 54

(±)-benzyl (4-chloro-3,6,7,8-tetrahydro-2H-indeno[4,5-b]furan-2-yl)methylcarbamate Treatment of (±)-1-(4-chloro-3,6,7,8-tetrahydro-2H-indeno[4,5-b]furan-2-yl)methanamine (1.11 g, 4.27 mmol) with diisopropylethylamine (1.65 g, 12.8 mmol) followed by benzyl chloroformate (0.87 g, 5.12 mmol) generally according to the procedure described for Intermediate 7 provided 1.5 g (98%) of (±)-benzyl (4-chloro-3,6,7,8-tetrahydro-2H-indeno[4,5-b]furan-2-yl)methylcarbamate as a white solid. mp 127-130° C.; Anal. calcd. for C$_{20}$H$_{20}$ClNO$_3$: C, 67.13; H, 5.63; N, 3.91. Found: C, 67.03; H, 5.42; N, 3.80. Chiral HPLC separation of (±)-benzyl (4-chloro-3,6,7,8-tetrahydro-2H-indeno[4,5-b]furan-2-yl)methylcarbamate (Chiralcel OD, methanol:water 9:1) provided two fractions. Fraction 1 (R$_t$=12.714 min Chiralcel OD, methanol:water 9:1); Fraction 2 (R$_t$=16.644 min, Chiralcel OD, methanol:water 9:1).

Intermediate 55

(±)-methyl (4-chloro-3,6,7,8-tetrahydro-2H-indeno[4,5-b]furan-2-yl)methylcarbamate Treatment of (±)-1-(4-chloro-3,6,7,8-tetrahydro-2H-indeno[4,5-b]furan-2-yl)methanamine hydrochloric salt (0.60 g, 2.3 mmol) with diisopropylethylamine (0.89 g, 6.9 mmol) and methyl chloroformate (0.44 g, 4.6 mmol) generally according to the procedure described for Intermediate 7 provided 0.6 g of (±)-methyl (4-chloro-3,6,7,8-tetrahydro-2H-indeno[4,5-b]furan-2-yl)methylcarbamate as white solid. mp 139-141° C.; Anal. calcd. for C$_{14}$H$_{16}$ClNO$_3$: C, 59.68; H, 5.72; N, 4.97. Found: C, 58.99; H, 5.72; N, 4.86.

Intermediate 56

(±)-3-[2-(benzyloxy)-5-chloro-3-methoxyphenyl]propane-1,2-diol

Treatment of 2-allyl-4-chloro-6-methoxyphenyl (20.0 g, 0.1 mol) with sodium hydride (4.7 g, 0.117 mol) and benzyl bromide (22.3 g, 0.13 mol) generally according to the procedure described for Intermediate 38 provided 28.0 g of 1-allyl-2-(benzyloxy)-5-chloro-3-methoxybenzene as a pale yellow oil. Treatment of the benzyl ether with AD-mix-α (132.0 g) generally according to the procedure described for Intermediate 2 afforded 20.2 (65%) g of (±)-3-[2-(benzyloxy)-5-chloro-3-methoxyphenyl]propane-1,2-diol as a white solid. mp. 65-68° C.; Anal. calcd. for C$_{17}$H$_{19}$ClO$_4$: C, 63.26; H, 5.93. Found: C, 75.17; H, 6.31.

Intermediate 57

(±)-(5-chloro-7-methoxy-2,3-dihydro-1-benzofuran-2-yl)methyl 4-methylbenzenesulfonate Treatment of (±)-3-[2-(benzyloxy)-5-chloro-3-methoxyphenyl]propane-1,2-diol (32.28 g, 0.1 mol) with p-toluenesulfonyl chloride (21 g, 0.11 mol) in pyridine (1000 mL) generally according to the procedure described for Intermediate 18 provided (±)-3-[2-(benzyloxy)-5-chloro-3-methoxyphenyl]-2-hydroxypropyl 4-methylbenzenesulfonate. Treatment of the tosylate with palladium on carbon (5 wt. %, 2.32 g) and hydrogen chloride (19 mL, 4.0 M in isopropanol) generally according to the procedure described for Intermediate 4 gave (±)-3-(5-chloro-2-hydroxy-3-methoxyphenyl)-2-hydroxypropyl 4-methylbenzenesulfonate. Treatment of the phenyl with triphenylphosphine (23.6 g, 0.09 mol) and diisopropyl azodicarboxylate (18.2 g, 0.09 mol) generally according to the procedure described for Intermediate 5 gave 28.2 g (76%) of (±)-(5-chloro-7-methoxy-2,3-dihydro-1-benzofuran-2-yl)methyl 4-methylbenzenesulfonate as a pale yellow solid. mp 99-102° C.; Anal. calcd. for C$_{17}$H$_{17}$ClO$_5$S: C, 55.36; H, 4.65. Found: C, 55.35; H, 4.62.

Intermediate 58

(±)-(6-allyl-5-chloro-7-hydroxy-2,3-dihydro-1-benzofuran-2-yl)methyl 4-methylbenzenesulfonate Treatment of (±)-(5-chloro-7-methoxy-2,3-dihydro-1-benzofuran-2-yl)methyl 4-methylbenzenesulfonate (22.1 g, 0.06 mol) with hydrogen bromide (30 wt. % in acetic acid, 400 mL) followed by potassium carbonate (4.15 g, 0.03 mol) provided (±)-(5-chloro-7-hydroxy-2,3-dihydro-1-benzofuran-2-yl)methyl 4-methylbenzenesulfonate as a brown oil. Treatment of the phenyl with sodium hydride (3.2 g, 0.053 mol) and allyl bromide (6.4 g, 0.053 mol) generally according to the procedure described for Intermediate 37 afforded (±)-[7-(allyloxy)-5-chloro-2,3-dihydro-1-benzofuran-2-yl]methyl 4-methylbenzenesulfonate. Treatment of the allyl ether in refluxing mesitylene (250 mL) generally according to the procedure described for Intermediate 1 afforded 4.5 g (19%) of (±)-(6-allyl-5-chloro-7-hydroxy-2,3-dihydro-1-benzofuran-2-yl)methyl 4-methylbenzenesulfonate as a pale yellow solid. mp 128-131° C.; Anal. calcd. for $C_{19}H_{19}ClO_5S$: C, 57.79; H, 4.85. Found: C, 58.28; H, 4.68.

Intermediate 59

(±)-(5-chloro-3,6,7,8-tetrahydro-2H-indeno[4,5-b]furan-2-yl)methyl 4-methylbenzenesulfonate Treatment of (±)-(6-allyl-5-chloro-7-hydroxy-2,3-dihydro-1-benzofuran-2-yl)methyl 4-methylbenzenesulfonate (4.5 g, 11.4 mmol) with diisopropylethylamine (2.18 mL, 12.5 mmol) followed by trifluoromethanesulfonic anhydride (2.11 g, 12.5 mmol) generally according to the procedure described for Intermediate 44 gave 4.8 g (81%) of (±)-(6-allyl-5-chloro-7-{[(trifluoromethyl)sulfonyl]oxy}-2,3-dihydro-1-benzofuran-2-yl)methyl 4-methylbenzenesulfonate as a brown oil. Treatment of the triflate with 9-borabicyclo[3.3.1]nonane (25 mL, 0.5 M in tetrahydrofuran) followed by dichloro[1,1'-bis(diphenylphosphino)ferrocene]palladium (II) dichloromethane adduct (0.3 g, 0.37 mmol), and potassium phosphate (2.96 g, 13.9 mmol) generally according to the procedure described for Intermediate 45 afforded 1.4 g (40%) of (±)-(5-chloro-3,6,7,8-tetrahydro-2H-indeno[4,5-b]furan-2-yl)methyl 4-methylbenzenesulfonate as a white solid. mp 82-84° C.; Anal. calcd. for $C_{19}H_{19}ClO_4S$: C, 60.23; H, 5.05. Found: C, 60.59; H, 5.06.

Intermediate 60

(±)-benzyl (5-chloro-3,6,7,8-tetrahydro-2H-indeno[4,5-b]furan-2-yl)methylcarbamate Treatment of (±)-1-(5-chloro-3,6,7,8-tetrahydro-2H-indeno[4,5-b]furan-2-yl)methanamine (0.51 g, 1.96 mmol) with diisopropylethylamine (0.76 g, 5.88 mmol) followed by benzyl chloroformate (0.50 g, 2.94 mmol) generally according to the procedure described for Intermediate 7 provided 0.58 g (84%) of (±)-benzyl (5-chloro-3,6,7,8-tetrahydro-2H-indeno[4,5-b]furan-2-yl)methylcarbamate as a white solid. mp 118-121° C.; Anal. calcd. for $C_{20}H_{20}ClNO_3$: C, 67.13; H, 5.63; N, 3.91. Found: C, 66.95; H, 5.93; N, 3.82. Chiral HPLC separation of (±)-benzyl (5-chloro-3,6,7,8-tetrahydro-2H-indeno[4,5-b]furan-2-yl)methylcarbamate (Chiralpak AD, hexane:isopropanol 9:1) provided two fractions. Fraction 1 ($R_t$=11.191 min, Chiralpak AD, hexane:isopropanol 9:1); Fraction 2 ($R_t$=12.735 min, Chiralpak AD, hexane:isopropanol 9:1).

EXAMPLE 1

(±)-1-(3,6,7,8-tetrahydro-2H-indeno[4,5-b]furan-2-yl)methanamine

To a solution of (±)-3,6,7,8-tetrahydro-2H-indeno[4,5-b]furan-2-ylmethanol (0.500 g, 2.63 mmol) in tetrahydrofuran (25 mL) was added triphenylphoshine (1.03 g, 3.94 mmol), phthalimide (0.58 g, 3.94 mmol) followed by diethylazodicarboxylate (0.687 g, 3.94 mmol) and the reaction mixture was allowed to stir at room temperature for 12 h. The reaction was quenched by the addition of water (5 mL) and the solvent was removed in vacuo. Purification by flash column chromatography (silica, ethyl acetate:hexanes 1:3) provided 0.65 g of (±)-2-(3,6,7,8-tetrahydro-2H-indeno[4,5-b]furan-2-ylmethyl)-1H-isoindole-1,3(2H)-dione as a white solid (mp 131-135° C.). The solid was re-dissolved in methanol (10 mL) and hydrazine monohydrate (0.153 g, 3.06 mmol) was added to the reaction mixture. The reaction mixture was heated at reflux for 12 h, concentrated hydrogen chloride (12.1 M, 3 mL) was added and heating was continued for an additional 1 h. The reaction mixture was cooled to room temperature and diluted with water (150 mL) and aqueous sodium hydroxide (2.5 N, 10 mL). The reaction mixture was extracted with ethyl acetate (2×75 mL) and the combined organic layers were dried (magnesium sulfate) and the solvent was removed in vacuo. Purification by flash column chromatography (silica, 10% aqueous ammonium hydroxide/methanol:ethyl acetate 1:19) provided a colorless oil. The oil was re-dissolved in isopropanol (1 mL) and hydrogen chloride (1.0 N in diethyl ether, 5 mL) was added. The resulting precipitate was filtered, washed (diethyl ether), and dried to afford 0.42 g (71%) of (±)-1-(3,6,7,8-tetrahydro-2H-indeno[4,5-b]furan-2-yl)methanamine as a white solid, hydrochloride salt. mp>230° C. (dec); Anal. calcd. for $C_{12}H_{15}NOHCl$: C, 63.85; H, 7.14; N, 6.21. Found: C, 63.64; H, 7.25; N, 6.02.

EXAMPLE 2

(±)-1-(3,6,7,8-tetrahydro-2H-indeno[4,5-b]furan-2-yl)methanamine

To a solution of 0.190 g of fraction 1 obtained from the chiral HPLC separation of (±)-benzyl 3,6,7,8-tetrahydro-2H-indeno[4,5-b]furan-2-ylmethylcarbamate (Chiralcel OJ, isopropanol:hexane 7:3) in ethanol (25 mL) was added palladium on carbon (10 wt. %, 0.05 g) and the reaction mixture was shaken under a hydrogen atmosphere (50 psi) for 4 h. The reaction mixture was filtered (celite) and the solvent removed in vacuo to provide a crude oil. The oil was re-dissolved in isopropanol (1 mL) and hydrogen chloride (1.0 N in diethyl ether, 5 mL) was added. The resulting precipitate was filtered, washed (diethyl ether), and dried to afford 0.102 g (76%) of (+)-1-(3,6,7,8-tetrahydro-2H-indeno[4,5-b]furan-2-yl)methanamine as a white solid, hydrochloride salt. $[\alpha]_D^{25}$=+39.00 (c 10.0 in methanol); Anal. calcd. for $C_{12}H_{15}NOHCl$: C, 63.85; H, 7.14; N, 6.21. Found: C, 63.87; H, 7.34; N, 6.14.

EXAMPLE 3

(−)-1-(3,6,7,8-tetrahydro-2H-indeno[4,5-b]furan-2-yl)methanamine

Treatment of 0.410 g of fraction 2 obtained from the chiral HPLC separation of (±)-benzyl 3,6,7,8-tetrahydro-2H-indeno[4,5-b]furan-2-ylmethylcarbamate (Chiralcel OJ, isopropanol:hexane 7:3) with palladium on carbon (10 wt. %, 0.05 g) generally according to the procedure described for Example 2 gave 0.235 g (83%) of (−)-1-(3,6,7,8-tetrahydro-2H-indeno[4,5-b]furan-2-yl)methanamine as a white solid, hydrochloride salt. $[\alpha]_D^{25}$=−39.98 (c 10.0 in methanol); Anal. calcd. for $C_{12}H_{15}NOHCl$: C, 63.85; H, 7.14; N, 6.21. Found: C, 63.81; H, 7.07; N, 6.14.

EXAMPLE 4

(±)-1-(2,3,6,7,8,9-hexahydronaphtho[1,2-b]furan-2-yl)methanamine

Treatment of (±)-2,3,6,7,8,9-hexahydronaphtho[1,2-b]furan-2-ylmethyl 4-methylbenzenesulfonate (2.05 g, 5.72 mmol) with sodium azide (0.929 g, 14.30 mmol) generally according to the procedure described for Intermediate 24 gave (±)-2-(azidomethyl)-2,3,6,7,8,9-hexahydronaphtho[1,2-b]furan. Treatment of the azide with palladium on carbon (10 wt. %, 0.094 g) generally according to the procedure described for Example 2 afforded 0.917 g (67%) of (±)-1-(2,3,6,7,8,9-hexahydronaphtho[1,2-b]furan-2-yl)methanamine as a white solid, hydrochloride salt. mp>220° C. (dec.); Anal. calcd. for $C_{13}H_{17}NOHCl·0.1H_2O$: C, 64.15; H, 7.50; N, 5.75. Found: C, 64.41; H, 7.64; N, 5.67.

EXAMPLE 5

(+)-1-(2,3,6,7,8,9-hexahydronaphtho[1,2-b]furan-2-yl)methanamine

Treatment of 0.285 g of fraction 1 obtained from the chiral HPLC separation of (±)-benzyl 2,3,6,7,8,9-hexahydronaphtho[1,2-b]furan-2-ylmethylcarbamate (Chiralcel OJ, isopropanol:hexane 9:1) with palladium on carbon (10 wt. %, 0.03 g) generally according to the procedure described for Example 2 afforded 0.088 g (43%) of (+)-1-(3,6,7,8-tetrahydro-2H-indeno[4,5-b]furan-2-yl)methanamine as a white solid, hydrochloride salt. $[\alpha]_D^{25}$=+35.2 (c 10.0 in methanol); mp>220° C. (dec); $^1$H NMR (DMSO-d$_6$) $^δ$H 8.12 (s, 3H); 6.91 (d, 1H); 6.56 (d, 1H); 4.96 (m, 1H); 3.29 (m, 1H); 3.14 (m, 1H); 2.95 (m, 2H); 2.65 (m, 2H); 2.5 (m, 2H); 1.70 (m, 4H).

EXAMPLE 6

(−)-1-(2,3,6,7,8,9-hexahydronaphtho[1,2-b]furan-2-yl)methanamine

Treatment of 0.650 g of fraction 2 obtained from the chiral HPLC separation of (±)-benzyl 2,3,6,7,8,9-hexahydronaphtho[1,2-b]furan-2-ylmethylcarbamate (Chiralcel OJ, isopropanol:hexane 9:1) with palladium on carbon (10 wt. %, 0.07 g) generally according to the procedure described for Example 2 afforded 0.326 g (70%) of (−)-1-(3,6,7,8-tetrahydro-2H-indeno[4,5-b]furan-2-yl)methanamine as a white solid, hydrochloride salt. $[\alpha]_D^{25}$=−37.8 (c 10.0 in methanol); mp>220° C. (dec); $^1$H NMR (DMSO-d$_6$) $δ_H$ 8.12 (s, 3H); 6.91 (d, 1H); 6.56 (d, 1H); 4.96 (m, 1H); 3.29 (m, 1H); 3.14 (m, 1H); 2.95 (m, 2H); 2.65 (m, 2H); 2.5 (m, 2H); 1.70 (m, 4H).

EXAMPLE 7

(±)-1-(5-methyl-3,6,7,8-tetrahydro-2H-indeno[4,5-b]furan-2-yl)methanamine

Treatment of (±)-(5-methyl-3,6,7,8-tetrahydro-2H-indeno[4,5-b]furan-2-yl)methyl 4-methylbenzenesulfonate (0.862 g, 2.40 mmol) with sodium azide (0.469 g, 7.21 mmol) generally according to the procedure described for Intermediate 24 gave (±)-(5-methyl-3,6,7,8-tetrahydro-2H-indeno[4,5-b]furan-2-yl)methyl azide. Treatment of the azide with palladium on carbon (10 wt. %, 0.055 g) generally according to the procedure described for Example 2 gave 0.460 g (80%) of (±)-1-(5-methyl-3,6,7,8-tetrahydro-2H-indeno[4,5-b]furan-2-yl)methanamine as a white solid, hydrochloride salt. mp>200° C. (dec.); Anal. calcd. for $C_{13}H_{17}NOHCl$: C, 65.13; H, 7.57; N, 5.84. Found: C, 64.97; H, 7.61; N, 5.67.

EXAMPLE 8

(+)-1-(5-methyl-3,6,7,8-tetrahydro-2H-indeno[4,5-b]furan-2-yl)methanamine

Treatment of (+)-benzyl (5-methyl-3,6,7,8-tetrahydro-2H-indeno[4,5-b]furan-2-yl)methylcarbamate (0.93 g, 2.74 mmol) with palladium on carbon (10%, 0.093 g) generally according to the procedure described for Example 2 afforded 0.427 g (65%) of (+)-1-(3,6,7,8-tetrahydro-2H-indeno[4,5-b]furan-2-yl)methanamine as a white solid, hydrochloride salt. $[\alpha]_D^{25}$=+48.0 (c 10.0 in methanol); mp>220° C.; Anal. calcd. for $C_{13}H_{17}NOHCl·0.1H_2O$: C, 64.64; H, 7.59; N, 5.80. Found: C, 64.63; H, 7.63; N, 5.76.

EXAMPLE 9

(−)-1-(5-methyl-3,6,7,8-tetrahydro-2H-indeno[4,5-b]furan-2-yl)methanamine

Treatment of (−)-benzyl (5-methyl-3,6,7,8-tetrahydro-2H-indeno[4,5-b]furan-2-ylmethylcarbamate (1.39 g, 4.12 mmol) with palladium on carbon (10 wt. %, 0.139 g) generally according to the procedure described for Example 2 afforded 0.862 g (87%) of (−)-1-(3,6,7,8-tetrahydro-2H-indeno[4,5-b]furan-2-yl)methanamine as a white solid, hydrochloride salt. $[\alpha]_D^{25}$=+48.6 (c 10.0 in methanol); mp>220° C.; Anal. calcd. for $C_{13}H_{17}NOHCl·0.1H_2O$: C, 64.64; H, 7.59; N, 5.80. Found: C, 64.62; H, 7.66; N, 5.77.

EXAMPLE 10

(±)-1-(2,3-dihydronaphtho[1,2-b]furan-2-yl)methanamine

Treatment of (±)-2-(azidomethyl)-2,3-dihydronaphtho[1,2-b]furan (1.61 g, 7.15 mmol) with palladium on carbon (10 wt. %, 0.160 g) generally according to the procedure described for Example 2 afforded 1.48 g (88%) of (±)-1-(2,3-dihydronaphtho[1,2-b]furan-2-yl)methanamine as a white solid, hydrochloride salt. mp>250° C. (dec.); Anal. calcd. for $C_{13}H_{13}NOHCl$: C, 66.24; H, 5.99; N, 5.94. Found: C, 66.23; H, 6.07; N, 5.77.

EXAMPLE 11

(+)-1-(2,3-dihydronaphtho[1,2-b]furan-2-yl)methanamine

Treatment of 0.83 g of fraction 1 obtained from the chiral HPLC separation of (±)-benzyl 2,3-dihydronaphtho[1,2-b]furan-2-ylmethylcarbamate (Chiralcel OJ, ethanol) with palladium on carbon (10 wt. %, 0.083 g) generally according to the procedure described for Example 2 provided 0.452 g (77%) of (+)-1-(2,3-dihydronaphtho[1,2-b]furan-2-yl)methanamine as a white solid, hydrochloride salt. $[\alpha]_D^{25}$=+10.85 (c 9.95 in methanol); mp>250° C.; Anal. calcd. for $C_{13}H_{13}NOHCl$: C, 66.24; H, 5.99; N, 5.94. Found: C, 66.03; H, 5.95; N, 5.87.

EXAMPLE 12

(−)-1-(2,3-dihydronaphtho[1,2-b]furan-2-yl)methanamine

Treatment of 1.22 g of fraction 2 obtained from the chiral HPLC separation of (±)-benzyl 2,3-dihydronaphtho[1,2-b]furan-2-ylmethylcarbamate (Chiralcel OJ, ethanol) with palladium on carbon (10 wt. %, 0.122 g) generally according to the procedure described for Example 2 provided 0.498 g (58%) of (−)-1-(2,3-dihydronaphtho[1,2-b]furan-2-yl)methanamine as a white solid, hydrochloride salt. $[\alpha]_D^{25}$=−13.23 (c 9.75 in methanol); mp>250° C.; Anal. calcd. for $C_{13}H_{13}NOHCl$: C, 66.24; H, 5.99; N, 5.94. Found: C, 65.88; H, 5.93; N, 5.86.

EXAMPLE 13

(±)-1-(2,3,5,6,7,8-hexahydronaphtho[2,3-b]furan-2-yl)methanamine

Treatment of (±)-benzyl 2,3,5,6,7,8-hexahydronaphtho[2,3-b]furan-2-ylmethylcarbamate (1.00 g, 2.96 mmol) with palladium on carbon (10 wt. %, 0.100 g) generally according to the procedure described for Example 2 provided 0.643 g (91%) of (±)-1-(2,3,5,6,7,8-hexahydronaphtho[2,3-b]furan-2-yl)methanamine as a white solid, hydrochloride salt. mp>225° C.; Anal. calcd. for $C_{13}H_{17}NOHCl$: C, 65.13; H, 7.57; N, 5.84. Found: C, 65.0; H, 7.87; N, 5.77.

EXAMPLE 14

(±)-1-(1,2,6,7,8,9-hexahydronaphtho[2,1-b]furan-2-yl)methanamine

Treatment of (±)-benzyl 1,2,6,7,8,9-hexahydronaphtho[2,1-b]furan-2-ylmethylcarbamate (1.00 g, 2.96 mmol) obtained from the chiral HPLC separation (Chiralcel OJ, ethanol) of (±)-benzyl 2,3,5,6,7,8-hexahydronaphtho[2,3-b]furan-2-ylmethylcarbamate and (±)-benzyl 1,2,6,7,8,9-hexahydronaphtho[2,1-b]furan-2-ylmethylcarbamate with palladium on carbon (10 wt. %, 0.100 g) generally according to the procedure described for Example 2 provided 0.455 g (64%) of (±)-1-(1,2,6,7,8,9-hexahydronaphtho[2,1-b]furan-2-yl)methanamine as a white solid, hydrochloride salt. mp>225° C.; Anal. calcd. for $C_{13}H_{17}NOHCl$: C, 65.13; H, 7.57; N, 5.84. Found: C, 64.64; H, 7.68; N, 5.8.

EXAMPLE 15

(9-methoxy-4-oxatetracyclo[9.2.1.0$^{2,10}$.0$^{3,7}$]tetradeca-2,7,9-trien-5-yl)methylamine Treatment of [(2R*,6R*,9S*)-5-methoxy-2,3,6,7,8,9-hexahydro-6,9-methanonaphtho[1,2-b]furan-2-yl]methyl 4-methylbenzenesulfonate (1.2 g, 2.30 mmol) with sodium azide (0.78 g, 11.99 mmol) generally according to the procedure described for Intermediate 24 gave (2R*,6R*,9S*)-2-(azidomethyl)-5-methoxy-2,3,6,7,8,9-hexahydro-6,9-methanonaphtho[1,2-b]furan. Treatment of the azide with palladium on carbon (10 wt. %, 0.10 g) generally according to the procedure described for Example 2 gave 0.45 g (53%) of (9-methoxy-4-oxatetracyclo[9.2.1.0$^{2,10}$.0$^{3,7}$]tetradeca-2,7,9-trien-5-yl)methylamine as a white solid, hydrochloride salt. mp>200° C. (dec); Anal. calcd. for $C_{16}H_{21}NO_2HCl$: C, 63.94; H, 7.15; N, 4.97. Found: C, 64.68; H, 7.63; N, 4.5. Separation of the stereoisomers of (9-methoxy-4-oxatetracyclo[9.2.1.0$^{2,10}$.0$^{3,7}$]tetradeca-2,7,9-trien-5-yl)methylamine provided three compounds with >99% optical purity.

EXAMPLE 16

Diastereoisomer of (9-methoxy-4-oxatetracyclo[9.2.1.0$^{2,}$$_{10}$.0$^{3,7}$]tetradeca-2,7,9-trien-5-yl)methylamine as a white solid, hydrochloride salt. $[\alpha]_D^{25}$=+77.00 (c 10.00 in methanol); mp>180° C. (dec); Anal. calcd. for $C_{15}H_{19}NO_2HCl$: C, 63.94; H, 7.15; N, 4.97. Found: C, 63.54; H, 7.21; N, 4.95.

EXAMPLE 17

Diastereoisomer of (9-methoxy-4-oxatetracyclo[9.2.1.0$^{2,}$$_{10}$.0$^{3,7}$]tetradeca-2,7,9-trien-5-yl)methylamine as a white solid, hydrochloride salt. $[\alpha]_D^{25}$=−74.5 (c 10.00 in methanol); mp>150° C. (dec); Anal. calcd. for $C_{15}H_{19}NO_2HCl.0.1H_2O$: C, 63.53; H, 7.18; N, 4.94. Found: C, 63.28; H, 7.07; N, 4.58.

EXAMPLE 18

Diastereoisomer of (9-methoxy-4-oxatetracyclo[9.2.1.0$^{2,}$$_{10}$.0$^{3,7}$]tetradeca-2,7,9-trien-5-yl)methylamine as a white solid, hydrochloride salt. $[\alpha]_D^{25}$=+7.3 (c 8.91 in methanol); mp>150° C. (dec); Anal. calcd. for $C_{15}H_{19}NO_2HCl.0.2H_2O$: C, 63.13; H, 7.21; N, 4.91. Found: C, 62.87; H, 6.93; N, 4.69.

EXAMPLE 19

(±)-1-(5-methoxy-2,3,6,7,8,9-hexahydro-6,9-ethanonaphtho[1,2-b]furan-2-yl)methanamine Treatment of (±)-(5-methoxy-2,3,6,7,8,9-hexahydro-6,9-ethanonaphtho[1,2-b]furan-2-yl)methyl 4-methylbenzenesulfonate (5.45 g, 13.1 mmol) with sodium azide (3.419 g, 52.6 mmol) generally according to the procedure described for Intermediate 24 gave (±)-2-(azidomethyl)-5-methoxy-2,3,6,7,8,9-hexahydro-6,9-ethanonaphtho[1,2-b]furan. Treatment of the azide with palladium on carbon (10 wt. %, 0.350 g) generally according to the procedure described for Example 2 gave 2.88 g (74%) of (±)-1-(5-methoxy-2,3,6,7,8,9-hexahydro-6,9-ethanonaphtho[1,2-b]furan-2-yl)methanamine as a white solid, hydrochloride salt. mp>210° C.; Anal. calcd. for $C_{16}H_{21}NO_2HCl$: C, 64.97; H, 7.5; N, 4.74. Found: C, 64.71; H, 7.69; N, 4.54.

EXAMPLE 20

(+)-1-(5-methoxy-2,3,6,7,8,9-hexahydro-6,9-ethanonaphtho[1,2-b]furan-2-yl)methanamine Treatment of (±)-1-(5-methoxy-2,3,6,7,8,9-hexahydro-6,9-ethanonaphtho[1,2-b]furan-2-yl)methanamine (2.5 g, 8.45 mmol) with diisopropylethylamine (2.73 g, 21.12 mmol) followed by benzyl chloroformate (1.73 g, 10.14 mmol) generally according to the procedure described for Intermediate 7 provided 3.08 g (93%) of (±)-benzyl (5-methoxy-2,3,6,7,8,9-hexahydro-6,9-ethanonaphtho[1,2-b]furan-2-yl)methylcarbamate as a colorless oil. Chiral HPLC separation of (±)-benzyl (5-methoxy-2,3,6,7,8,9-hexahydro-6,9-ethanonaphtho[1,2-b]furan-2-yl)methylcarbamate (Chiralcel OJ, methanol) provided two fractions. Fraction 1 ($R_t$=13.252 min, Chiralcel OJ, methanol); Fraction 2 ($R_t$=18.196 min, Chiralcel OJ, methanol). Treatment of 0.460 g of fraction 1 obtained from the chiral HPLC separation of (±)-benzyl (5-methoxy-2,3,6,7,8,9-hexahydro-6,9-ethanonaphtho[1,2-b]furan-2-yl)methylcarbamate (Chiralcel OJ, methanol) with palladium on carbon (10 wt. %, 0.05 g) generally according to the procedure described for Example 2 provided 0.304 g (88%) of (+)-1-(5-methoxy-2,3,6,7,8,9-hexahydro-6,9-ethanonaphtho[1,2-b]furan-2-yl)methanamine as a white solid, hydrochloride salt. $[\alpha]_D^5$=+40.03 (c 9.99 in methanol); mp>220° C.; Anal. calcd. for $C_{16}H_{21}NO_2HCl$: C, 64.97; H, 7.5; N, 4.74. Found: C, 64.62; H, 7.79; N, 4.54.

EXAMPLE 21

(−)-1-(5-methoxy-2,3,6,7,8,9-hexahydro-6,9-ethanonaphtho[1,2-b]furan-2-yl)methanamine Treatment of 1.91 g of fraction 2 obtained from the chiral HPLC separation of (±)-benzyl (5-methoxy-2,3,6,7,8,9-hexahydro-6,9-ethanonaphtho[1,2-b]furan-2-yl)methylcarbamate (Chiralcel OJ, methanol) with palladium on carbon (10 wt. %, 0.20 g) generally according to the procedure described for Example 2 provided 1.18 g (82%) of (−)-1-(5-methoxy-2,3,6,7,8,9-hexahydro-6,9-ethanonaphtho[1,2-b]furan-2-yl)methanamine as a white solid, hydrochloride salt. $[\alpha]_D^{25}$=−40.98 (c 10.01 in methanol); mp>220° C.; Anal. calcd. for $C_{16}H_{21}NO_2HCl$: C, 64.97; H, 7.5; N, 4.74. Found: C, 64.61; H, 7.56; N, 4.53.

EXAMPLE 22

(2R*)-1-[(2R*)-3,6,7,8-tetrahydro-2H-indeno[4,5-b]furan-2-yl]ethylamine

To a solution of indan-4-ol (6.71 g, 50.00 mmol) in toluene (500 mL) cooled to 0° C. was added triphenylphosphine (14.43 g, 55.00 mmol) followed by diethylazodicarboxylate (9.58 g, 55.00 mmol) and finally 3-buten-2-ol (3.97 g, 55.00 mmol). The reaction mixture was allowed to stir at room temperature for 3 h. The reaction mixture was quenched by the addition of water (10 mL) and the solvent was removed in vacuo to give a crude solid. Purification by flash column chromatography (silica, ethyl acetate:hexanes 1:99) gave (±)-4-[(1-methylprop-2-enyl)oxy]indane. Treatment of the allyl ether in refluxing mesitylene generally according to the procedure described for Intermediate 1 afforded 5-[(2E)-but-2-enyl]indan-4-ol. To a solution of the olefin (7.74 g, 41.1 mmol) in dichloromethane (400 mL) cooled to 0° C. was added 3-chloroperoxybenzoic acid (25.34 g, 0.103 mol). The reaction mixture was allowed to stir at room temperature for 4 h. The solvent was removed in vacuo and the residue was re-dissolved in methanol (400 mL). Potassium carbonate (28.42 g, 0.206 mol) was added and the reaction mixture was allowed to stir at room temperature for 1 h. The solvent was removed in vacuo and the residue was partitioned between ethyl acetate (250 mL) and water (500 mL). The aqueous layer was extracted with ethyl acetate (250 mL) and the combined organic layers were washed with water (2×250 mL), saturated aqueous sodium chloride (200 mL), dried (magnesium sulfate), and the solvent was removed in vacuo to provide a crude oil. Purification by flash column chromatography (silica, ethyl acetate:hexanes 2:3) afforded (2S*)-1-[(2R*)-3,6,7,8-tetrahydro-2H-indeno[4,5-b]furan-2-yl]ethylamine. Treatment of the alcohol (3.05 g, 14.93 mmol) with p-toluenesulfonyl chloride (4.27 g, 22.40 mmol) in pyridine (150 mL) generally according to the procedure described for Intermediate 18 gave (1S*)-1-methyl-2-[(2R*)-3,6,7,8-tetrahydro-2H-indeno[4,5-b]furan-2-yl]ethyl 4-methylbenzenesulfonate. Treatment of the tosylate (4.55 g, 12.7 mmol) with sodium azide (3.30 g, 50.8 mmol) generally according to the procedure described for Intermediate 24 afforded (2R*)-2-[(2S*)-2-azidopropyl]-3,6,7,8-tetrahydro-2H-indeno[4,5-b]furan. Treatment of the azide with palladium on carbon (10 wt. %, 0.290 g) generally according to the procedure described for Example 2 gave 2.29 g (75%) of (2R*)-1-[(2R*)-3,6,7,8-tetrahydro-2H-indeno[4,5-b]furan-2-yl]ethylamine as a white solid, hydrochloride salt. mp>250° C.; Anal. calcd. for $C_{13}H_{17}NOHCl$: C, 65.13; H, 7.57; N, 5.84. Found: C, 65.16; H, 7.69; N, 5.63.

EXAMPLE 23

(±)-1-(5-chloro-2,3-dihydronaphtho[1,2-b]furan-2-yl)methanamine

Treatment of (±)-3-[1-(benzyloxy)-4-chloro-2-naphthyl]-2-hydroxypropyl 4-methylbenzenesulfonate (4.6 g, 9.26 mmol) with palladium on carbon (5 wt. %, 0.50 g) and hydrogen chloride in isopropanol (4.0 M, 4.0 mL) generally according to the procedure described for Intermediate 4 provided (±)-3-(4-chloro-1-hydroxy-2-naphthyl)-2-hydroxypropyl 4-methylbenzenesulfonate. Treatment of the phenyl with triphenylphosphine (3.5 g, 13.3 mmol) followed by diisopropylazodicarboxylate (2.69 g, 13.3 mmol) generally according to the procedure described for Intermediate 5 afforded (±)-(5-chloro-2,3-dihydronaphtho[1,2-b]furan-2-yl)methyl 4-methylbenzenesulfonate as a colorless oil. Treatment of the tosylate with sodium azide (1.1 g, 16.4 mmol) generally according to the procedure described for Intermediate 24 gave (±)-(5-chloro-2,3-dihydronaphtho[1,2-b]furan-2-yl) methyl azide as a pale brown oil. Treatment of the azide with sulfided platinum on carbon (5 wt. %, 0.15 g) generally according to the procedure described for Example 2 provided 1.07 g (43%) of (±)-1-(5-chloro-2,3-dihydronaphtho[1,2-b]furan-2-yl)methanamine as a white solid, hydrochloride salt. mp 269-271° C.; Anal. calcd. for $C_{13}H_{12}ClNOHCl.0.8H_2O$: C, 54.87; H, 5.17; N, 4.92. Found: C, 54.68; H, 4.78; N, 4.79.

EXAMPLE 24

(±)-1-(5-chloro-2,3-dihydronaphtho[1,2-b]furan-2-yl)-N-methylmethanamine

To a suspension of lithium aluminum hydride (95 wt. %, 0.45 g, 11.25 mmol) in tetrahydrofuran (45 mL) was added (±)-methyl (5-chloro-2,3-dihydronaphtho[1,2-b]furan-2-yl) methylcarbamate (1.16 g, 3.98 mmol) and the resulting reaction mixture was allowed to stir at room temperature for 40 h. The reaction mixture was diluted with tetrahydrofuran (150 mL), quenched with saturated ammonium chloride (50 mL), and the organic layer was separated and washed with saturated aqueous sodium bicarbonate (50 mL), saturated aqueous sodium chloride (50 mL), dried (magnesium sulfate), and the solvent was removed in vacuo to provide a crude oil. Purification by flash chromatography (silica, methanol:dichloromethane 1:39) provided a light brown oil. The oil was re-dissolved in tetrahydrofuran (50 mL) and aqueous hydrogen chloride (1.0 N, 1 mL) was added. The resulting precipitate was filtered, washed (diethyl ether), and dried to afford 0.23 g (20%) of (±)-1-(5-chloro-2,3-dihydronaphtho[1,2-b]furan-2-yl)-N-methylmethanamine as a white solid, hydrochloride salt. mp 224-226° C.; Anal. calcd. for $C_{14}H_{14}ClNOHCl.0.1H_2O$: C, 58.80; H, 5.36; N, 4.90. Found: C, 58.65; H, 5.30; N, 4.84.

EXAMPLE 25

(±)-1-(4-chloro-3,6,7,8-tetrahydro-2H-indeno[4,5-b]furan-2-yl)methanamine

Treatment of (±)-(4-chloro-3,6,7,8-tetrahydro-2H-indeno[4,5-b]furan-2-yl)methyl 4-methylbenzenesulfonate (4.0 g, 10.6 mmol) with sodium azide (2.75 g, 42.2 mmol) generally according to the procedure described for Intermediate 24 gave (±)-(4-chloro-3,6,7,8-tetrahydro-2H-indeno[4,5-b]furan-2-yl)methyl azide. Treatment of the azide with sulfided platinum on carbon (5 wt. %, 0.63 g) followed by hydrogen chloride (3 mL, 4 M in isopropanol) generally according to the procedure described for Example 2 provided 2.1 g (76%) of (±)-1-(4-chloro-3,6,7,8-tetrahydro-2H-indeno[4,5-b]furan-2-yl)methanamine as a white solid, hydrochloride salt. mp 251-254° C.; Anal. calcd. for $C_{12}H_{14}ClNOHCl$: C, 55.40; H, 5.81; N, 5.38. Found: C, 55.10; H, 5.68; N, 5.29.

EXAMPLE 26

(−)-1-(4-chloro-3,6,7,8-tetrahydro-2H-indeno[4,5-b]furan-2-yl)methanamine

Treatment of 0.34 g of fraction 1 obtained from the chiral HPLC separation of (±)-benzyl (4-chloro-3,6,7,8-tetrahydro-2H-indeno[4,5-b]furan-2-yl)methylcarbamate (Chiralcel OD, methanol:water 9:1) with palladium on carbon (5 wt. %, 0.13 g) and hydrogen chloride (4.0 M in isopropanol, 0.7 mL) generally according to the procedure described for Example 2 gave 0.23 g (93%) of (−)-1-(4-chloro-3,6,7,8-tetrahydro-2H-indeno[4,5-b]furan-2-yl)methanamine as a white solid, hydrochloride salt. mp 265-268° C.; $[\alpha]_D^{25}$=−51.96 (c 10 in methanol); Anal. calcd. for $C_{12}H_{14}ClNOHCl.0.5H_2O$: C, 53.55; H, 5.99; N, 5.20. Found: C, 53.50; H, 5.59; N, 4.99.

EXAMPLE 27

(+)-1-(4-chloro-3,6,7,8-tetrahydro-2H-indeno[4,5-b]furan-2-yl)methanamine

Treatment of 0.26 g of fraction 2 obtained from the chiral HPLC separation of (±)-benzyl (4-chloro-3,6,7,8-tetrahydro-2H-indeno[4,5-b]furan-2-yl)methylcarbamate (Chiralcel OD, methanol:water 9:1) with palladium on carbon (5 wt. %, 0.10 g) and hydrogen chloride (4.0 M in isopropanol, 0.7 mL) generally according to the procedure described for Example 2 gave 0.18 g (95%) of (+)-1-(4-chloro-3,6,7,8-tetrahydro-2H-indeno[4,5-b]furan-2-yl)methanamine as a white solid, hydrochloride salt. mp 265-268° C.; $[\alpha]_D^{25}$=+54.02° (c 10 in methanol); Anal. calcd. for $C_{12}H_{14}ClNOHCl.0.5H_2O$: C, 53.55; H, 5.99; N, 5.20. Found: C, 53.27; H, 5.54; N, 5.01.

EXAMPLE 28

(±)-1-(4-chloro-3,6,7,8-tetrahydro-2H-indeno[4,5-b]furan-2-yl)-N-methylmethanamine Treatment of (±)-methyl (4-chloro-3,6,7,8-tetrahydro-2H-indeno[4,5-b]furan-2-yl)methylcarbamate (0.60 g, 2.12 mmol) with lithium aluminum hydride (95 wt. %, 0.35 g, 8.75 mmol) generally according to the procedure described for Example 24 provided 0.15 g (30%) of (±)-1-(4-chloro-3,6,7,8-tetrahydro-2H-indeno[4,5-b]furan-2-yl)-N-methylmethanamine as a white solid. mp 58-60° C.; Anal. calcd. for $C_{13}H_{16}ClNO$: C, 65.68; H, 6.78; N, 5.89. Found: C, 65.31; H, 6.79; N, 5.52.

EXAMPLE 29

(±)-1-(5-chloro-3,6,7,8-tetrahydro-2H-indeno[4,5-b]furan-2-yl)methanamine

Treatment of (±)-(5-chloro-3,6,7,8-tetrahydro-2H-indeno[4,5-b]furan-2-yl)methyl 4-methylbenzenesulfonate (1.4 g, 3.70 mmol) with sodium azide (0.96 g, 14.78 mmol) generally according to the procedure described for Intermediate 24 gave (±)-(5-chloro-3,6,7,8-tetrahydro-2H-indeno[4,5-b]furan-2-yl)methyl azide as a crude oil. Treatment of the azide with sulfided platinum on carbon (5 wt. %, 0.15 g) generally according to the procedure described for Example 2 provided 0.74 g (77%) of (±)-1-(5-chloro-3,6,7,8-tetrahydro-2H-indeno[4,5-b]furan-2-yl)methanamine as a white solid, hydrochloride salt. mp 270° C. (dec); Anal. calcd. for $C_{12}H_{14}ClNOHCl$: C, 55.4; H, 5.81; N, 5.38. Found: C, 55.4; H, 5.8; N, 4.91.

EXAMPLE 30

(−)-1-(5-chloro-3,6,7,8-tetrahydro-2H-indeno[4,5-b]furan-2-yl)methanamine

To 0.3 g of fraction 1 obtained from the chiral HPLC separation of (±)-benzyl (5-chloro-3,6,7,8-tetrahydro-2H-indeno[4,5-b]furan-2-yl)methylcarbamate (Chiralpak AD, hexane:isopropanol 9:1) was added hydrogen bromide (30 wt. % in acetic acid, 7 mL) and the reaction mixture was allowed to stir for 1 h. The reaction mixture was diluted with diethyl ether (20 mL) and the resulting precipitate was filtered, washed (diethyl ether), and dried to provide 0.192 g (76%) of (−)-1-(5-chloro-3,6,7,8-tetrahydro-2H-indeno[4,5-b]furan-2-yl)methanamine as a white solid, hydrobromide salt. mp>330° C.; $[\alpha]_D^5$=−43.5° (c 10 in methanol); Anal. calcd. for $C_{12}H_{14}ClNOHBr$: C, 47.32; H, 4.96; N, 4.6. Found: C, 46.97; H, 4.76; N, 4.5.

EXAMPLE 31

(+)-1-(5-chloro-3,6,7,8-tetrahydro-2H-indeno[4,5-b]furan-2-yl)methanamine

Treatment of 0.12 g of fraction 2 obtained from the chiral HPLC separation of (+)-benzyl (5-chloro-3,6,7,8-tetrahydro-2H-indeno[4,5-b]furan-2-yl)methylcarbamate (Chiralpak AD, hexane:isopropanol 9:1) with hydrogen bromide (30 wt. % in acetic acid, 7 mL) generally according to the procedure described for Example 30 gave 0.066 g (64%) of (+)-1-(5-chloro-3,6,7,8-tetrahydro-2H-indeno[4,5-b]furan-2-yl)methanamine as a white solid, hydrobromide salt. mp>330° C.; $[\alpha]_D^{25}$=+42.9° (c 10 in methanol); Anal. calcd. for $C_{12}H_{14}ClNOHBr$: C, 47.32; H, 4.96; N, 4.6. Found: C, 46.98; H, 4.77; N, 4.55.

EXAMPLE 32

Determination of Binding Affinity and Agonist Activity of Compounds of Formula 1

The ability of the compounds of this invention to act as $5HT_{2C}$ agonists and partial agonists was established using several standard pharmacological test procedures; the procedures used and results obtained are provided below. In the test procedures, 5-HT stands for 5-hydroxytryptamine, mCPP stands for meta-chlorophenylpiperazine, and DOI stands for 1-(2,5-dimethoxy-4-iodophenyl)isopropylamine.

To evaluate the affinity of various compounds of formula 1 for the $5-HT_{2C}$ receptor, a CHO (Chinese Hamster Ovary) cell line transfected with the cDNA expressing the human 5-hydroxytryptamine-2C ($h5-HT_{2C}$) receptor was maintained in DMEM (Dulbecco's Modified Eagle Media) supplied with fetal calf serum, glutamine, and the markers: guaninephosphoribosyl transferase (GTP), and hypoxanthinethymidine (HT). The cells were allowed to grow to confluence in large culture dishes with intermediate changes of media and splitting. Upon reaching confluence, the cells were harvested by scraping. The harvested cells were suspended in half volume of fresh physiological phosphate buffered saline (PBS) solution and centrifuged at low speed (900×g). This operation was repeated once. The collected cells were then homogenized with a polytron at setting #7 for 15 sec in ten volumes of 50 mM Tris.HCl, pH 7.4 and 0.5 mM EDTA. The homogenate was centrifuged at 900×g for 15 min to remove nuclear particles and other cell debris. The pellet was discarded and the supernatant fluid recentrifuged at 40,000×g for 30 min. The resulting pellet was resuspended in a small volume of Tris.HCl buffer and the tissue protein content was determined in aliquots of 10-25 microliter (μL) volumes. Bovine Serum Albumin (BSA) was used as the standard in the protein determination by the method of Lowry et al., (J. Biol. Chem., 193:265 (1951). The volume of the suspended cell membranes was adjusted with 50 mM Tris.HCl buffer containing: 0.1% ascorbic acid, 10 mM pargyline and 4 mM $CaCl_2$ to give a tissue protein concentration of 1-2 mg per ml of suspension. The preparation membrane suspension (many times concentrated) was aliquoted in 1 ml volumes and stored at −70° C. until used in subsequent binding experiments.

Binding measurements were performed in a 96 well microtiter plate format, in a total volume of 200 μL. To each well was added: 60 μL of incubation buffer made in 50 mM Tris.HCl buffer, pH 7.4 and containing 4 mM $CaCl_2$; 20 μL of [$^{125}$I] DOI (S.A., 2200 Ci/mmol, NEN Life Science).

The dissociation constant, KD of [$^{125}$I] DOI at the human serotonin 5-$HT_{2C}$ receptor was 0.4 nM by saturation binding with increasing concentrations of [$^{125}$I] DOI. The reaction was initiated by the final addition of 100 μL of tissue suspension containing 50 μg of receptor protein. Nonspecific binding was measured in the presence of 1 μM unlabeled DOI added in 20.0 μL volume. Test compounds were added in 20.0 μL. The mixture was incubated at room temperature for 60 min. The incubation was stopped by rapid filtration. The bound ligand-receptor complex was filtered off on a 96 well unifilter with a Packard® Filtermate 196 Harvester. The bound complex caught on the filter disk was dried in a vacuum oven heated to 60° C. and the radioactivity was measured by liquid scintillation with 40 μL Microscint-20 scintillant in a Packard TopCount® equipped with six (6) photomultiplier detectors.

Specific binding is defined as the total radioactivity bound less the amount bound in the presence of 1 μM unlabeled DOI. Binding in the presence of varying concentrations of test drugs is expressed as percent of specific binding in the absence of drug. These results are then plotted as log % bound vs. log concentration of test drug. Non linear regression analysis of data points yields both the $IC_{50}$ and the $K^i$ values of test compounds with 95% confidence limits. Alternatively, a linear regression line of decline of data points is plotted, from which the $IC_{50}$ value can be read off the curve and the $K_i$ value determined by solving the following equation:

$$K_i = \frac{IC_{50}}{1 + L/K_D}$$

where L is the concentration of the radioactive ligand used and the $K_D$ is the dissociation constant of the ligand for the receptor, both expressed in nM.

The following $K_i$'s (95% confidence interval) are provided for various reference compounds:

| Compound | $K_i$ |
| --- | --- |
| Ritanserin | 2.0 (1.3-3.1) nM |
| Ketanserin | 94.8 (70.7-127.0) nM |
| Mianserin | 2.7 (1.9-3.8) nM |
| Clozapine | 23.2 (16.0-34.0) nM |
| Methiothepin | 4.6 (4.0-6.0) nM |
| Methysergide | 6.3 (4.6-8.6) nM |
| Loxapine | 33.0 (24.0-47.0) nM |
| mCPP | 6.5 (4.8-9.0) nM |
| DOI | 6.2 (4.9-8.0) nM |

The ability of the compounds of formula 1 to produce an agonist response at brain 5-$HT_{2C}$ was assessed by determining their effect on calcium mobilization using the following procedure: CHO cells stably expressing the human 5-$HT_{2C}$ receptor were cultured in Dulbecco's modified Eagle's medium (DMEM) supplemented with 10% fetal bovine serum and non-essential amino acids. Cells were plated at a density of 40K cells/well in 96-well clear-bottom black-wall plates 24 hours prior to the evaluation of 5-$HT_{2C}$ receptor-stimulated calcium mobilization. For calcium studies, cells were loaded with the calcium indicator dye Fluo-3-AM in Hank's buffered saline (HBS) for 60 minutes at 37° C. Cells were washed with HBS at room temperature and transferred to the fluorometric imaging plate reader (FLIPR, Molecular Devices, Sunnyvale, Calif.) for acquisition of calcium images. Excitation at 488 nm was achieved with an Argon ion laser and a 510-560 nm emission filter was used. Fluorescence images and relative intensities were captured at 1 second intervals and cells were stimulated by addition of agonist after 10 baseline measurements using the internal fluidics module of the FLIPR. An increase in fluorescence counts corresponds to an increase in intracellular calcium.

For the evaluation of agonist pharmacology, the calcium changes in response to different concentrations of agonist were determined using a maximum minus minimum calculation of the raw fluorescence count data. Calcium changes were then expressed as a percentage of the response observed with a maximally effective concentration of 5-HT, and $EC_{50}$ values were estimated by non-linear regression analysis of the log-concentration % maximum 5-HT response curves using the 4-parameter logistic function.

The following $EC_{50}$'s are provided for various reference compounds:

| Compound | $EC_{50}$ |
| --- | --- |
| 5-HT | 0.5 nM |
| DOI | 0.5 nM |
| mCPP | 5.4 nM |

The results of the standard experimental test procedures described in the preceding paragraphs were as follows:

| | 5-$HT_{2C}$ Affinity | 5-$HT_{2C}$ Function | |
| --- | --- | --- | --- |
| Compound | $K_i$ (nM) | $EC_{50}$ (nM) | Emax (%) |
| Example 1 | 10 | 31 | 90 |
| Example 2 | 28 | 8 | 75 |
| Example 3 | 5 | 0.9 | 100 |
| Example 4 | 8 | 76 | 80 |
| Example 5 | 17 | 38 | 70 |
| Example 6 | 11 | 3 | 100 |

-continued

| Compound | 5-HT$_{2C}$ Affinity K$_i$ (nM) | 5-HT$_{2C}$ Function EC$_{50}$ (nM) | Emax (%) |
|---|---|---|---|
| Example 7 | 6 | 19 | 95 |
| Example 8 | 6 | 8.3 | 100 |
| Example 9 | 11 | 11 | 100 |
| Example 10 | 29 | 20 | 90 |
| Example 11 | 15 | 5.7 | 65 |
| Example 12 | 16 | 2 | 90 |
| Example 13 | 99 | | |
| Example 14 | 19 | 34 | 100 |
| Example 15 | 9 | 17 | 100 |
| Example 16 | 85 | | |
| Example 17 | 8 | 10 | 100 |
| Example 18 | 82 | | |
| Example 19 | 7 | 25 | 100 |
| Example 20 | 22 | 91 | 60 |
| Example 21 | 4 | 0.8 | 90 |
| Example 22 | 13 | 15 | 80 |
| Example 23 | 5 | 28 | 90 |
| Example 24 | 7 | 91 | 60 |
| Example 25 | 12 | 4.4 | 80 |
| Example 26 | 16 | 88 | 80 |
| Example 27 | 4 | 56 | 60 |
| Example 28 | 11 | | |
| Example 29 | 4 | 5.8 | 100 |
| Example 30 | 6 | 234 | 80 |
| Example 31 | 1 | 10 | 40 |

The entire disclosure of each patent, patent application, and publication cited or described in this document is hereby incorporated by reference.

We claim:

1. A compound of formula 1:

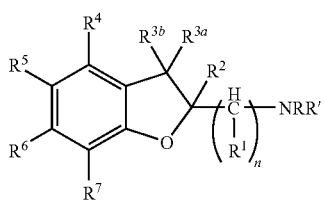

Formula 1 or pharmaceutically acceptable salts thereof;
wherein
R and R' are, independently, hydrogen, or unsubstituted alkyl of 1 to 6 carbon atoms;
alternatively R and R' can be taken together with the nitrogen to which they are attached to form a ring containing 2-5 carbon atoms;
$R^1$ and $R^2$ are each, independently, hydrogen, alkyl of 1 to 6 carbon atoms, cycloalkyl of 3 to 6 carbon atoms, or perfluoroalkyl of 1 to 6 carbon atoms;
$R^{3a}$ and $R^{3b}$ are, independently, hydrogen, halogen, hydroxyl, alkyl of 1 to 6 carbon atoms, perfluoroalkyl of 1 to 6 carbon atoms, alkoxy of 1 to 6 carbon atoms, or perfluoroalkoxy of 1 to 6 carbon atoms;
two adjacent substituents selected from $R^4$ and $R^5$, or $R^5$ and $R^6$, or $R^6$ and $R^7$, together with the carbon atoms to which they are attached, form a monocyclic cycloalkyl of 3 to 8 carbon atoms optionally substituted at a single carbon atom with a cycloalkyl of 3 to 5 carbon atoms;
the remaining $R^4$ to $R^7$ substituents are, independently, hydrogen, halogen, cyano, hydroxyl, carboxyl, alkyl of 1 to 8 carbon atoms, perfluoroalkyl of 1 to 6 carbon atoms, alkoxy of 1 to 6 carbon atoms, perfluoroalkoxy of 1 to 6 carbon atoms, aryl of 5 to 10 carbon atoms, aryloxy of 5 to 10 carbon atoms, alkenyl of 2 to 8 carbon atoms, alkanoyl of 2 to 6 carbon atoms, alkanoyloxy of 2 to 6 carbon atoms, carboalkoxy of 2 to 6 carbon atoms, carboxamido, alkanamido of 2 to 6 carbon atoms, alkanesulfonamido of 1 to 6 carbon atoms, amino, monoalkylamino of 1 to 6 carbon atoms, dialkylamino of 1 to 6 carbon atoms per alkyl moiety, cycloalkyl of 3 to 8 carbon atoms; and n is 1, 2 or 3;

wherein any cycloalkyl group is saturated or partially saturated, and any aryl, or cycloalkyl, group may optionally be substituted with 1 to 5 substituents independently selected from halogen, hydroxyl, alkyl of 1 to 6 carbon atoms, perfluoroalkyl of 1 to 6 carbon atoms, alkoxy of 1 to 6 carbon atoms, or perfluoroalkoxy of 1 to 6 carbon atoms.

2. A compound of claim 1 wherein $R^1$ and $R^2$ are each hydrogen or alkyl of 1 to 6 carbon atoms.

3. A compound of claim 1 wherein $R^{3a}$ and $R^{3b}$ are each hydrogen or alkyl of 1 to 6 carbon atoms.

4. A compound of claim 1 wherein the remaining $R^4$ to $R^7$ substituents are each independently, hydrogen, halogen, alkyl of 1 to 8 carbon atoms, alkoxy of 1 to 6 carbon atoms, aryloxy of 5 to 10 carbon atoms, cycloalkyl of 3 to 8 carbon atoms, or aryl of 5 to 10 carbon atoms.

5. A compound of claim 1, wherein $R^4$ and $R^5$ are, independently, hydrogen, halogen, alkyl of 1 to 8 carbon atoms, or alkoxy of 1 to 6 carbon atoms, and $R^6$ and $R^7$, together with the carbon atoms to which they are attached, form a monocyclic cycloalkyl of 3 to 8 carbon atoms.

6. A compound of claim 1 wherein $R^6$ and $R^7$, together with the carbon atoms to which they are attached, form a monocyclic cycloalkyl of 3 to 8 carbon atoms optionally substituted with one to five susbtituents, each independently selected from, alkyl, halogen, or alkoxy groups.

7. A compound of claim 6, wherein $R^4$ and $R^5$ are, independently hydrogen, alkyl of 1 to 6 carbon atoms, alkoxy of 1 to 4 carbon atoms, or halogen.

8. A compound of claim 7, wherein $R^1$ and $R^2$ are each hydrogen or alkyl of 1 to 6 carbon atoms.

9. A compound of claim 1, wherein $R^6$ and $R^7$, together with the carbon atoms to which they are attached, form monocyclic cycloalkyl of 3 to 8 carbon atoms optionally substituted with one to five susbtituents, each independently selected from alkyl groups of 1 to 6 carbon atoms, halogens, or alkoxy groups of 1 to 6 carbon atoms.

10. A compound of claim 9, wherein $R^4$ and $R^5$ are, independently, hydrogen, alkyl of 1 to 6 carbon atoms, alkoxy of 1 to 4 carbon atoms, or halogen.

11. A compound of claim 10 wherein R, R', $R^1$, and $R^2$ are each hydrogen.

12. A compound of claim 1, wherein n is 1, R' is hydrogen, and $R^1$ and $R^2$ are, independently, hydrogen, alkyl of 1 to 6 carbon atoms, or perfluoroalkyl of 1 to 6 carbon atoms.

13. A compound of formula 1:

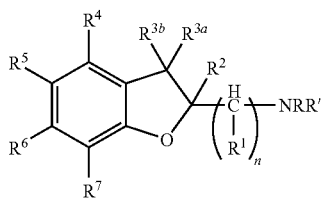

Formula 1 or pharmaceutically acceptable salts thereof;
wherein
R and R' are, independently, hydrogen, alkyl of 1 to 6 carbon atoms;
alternatively R and R' can be taken together with the nitrogen to which they are attached to form a ring containing 2-5 carbon atoms;
$R^1$ and $R^2$ are each, independently, hydrogen, alkyl of 1 to 6 carbon atoms, cycloalkyl of 3 to 6 carbon atoms, or perfluoroalkyl of 1 to 6 carbon atoms;
$R^{3a}$ and $R^{3b}$ are, independently, hydrogen, halogen, hydroxyl, alkyl of 1 to 6 carbon atoms, perfluoroalkyl of 1 to 6 carbon atoms, alkoxy of 1 to 6 carbon atoms, or perfluoroalkoxy of 1 to 6 carbon atoms;
two adjacent substituents selected from $R^4$ and $R^5$, or $R^5$ and $R^6$, or $R^6$ and $R^7$, together with the carbon atoms to which they are attached, form a monocyclic cycloalkyl of 3 to 8 carbon atoms; and
the remaining $R^4$ to $R^7$ substituents are, independently, hydrogen, halogen, cyano, hydroxyl, carboxyl, alkyl of 1 to 8 carbon atoms, perfluoroalkyl of 1 to 6 carbon atoms, alkoxy of 1 to 6 carbon atoms, perfluoroalkoxy of 1 to 6 carbon atoms, alkenyl of 2 to 8 carbon atoms, alkanoyl of 2 to 6 carbon atoms, alkanoyloxy of 2 to 6 carbon atoms, carboalkoxy of 2 to 6 carbon atoms, carboxamido, alkanamido of 2 to 6 carbon atoms, alkanesulfonamido of 1 to 6 carbon atoms, amino, monoalkylamino of 1 to 6 carbon atoms, or dialkylamino of 1 to 6 carbon atoms per alkyl moiety;
wherein any cycloalkyl, and any aryl or cycloalkyl, group may optionally be substituted with 1 to 5 substituents independently selected from halogen, hydroxyl, alkyl of 1 to 6 carbon atoms, perfluoroalkyl of 1 to 6 carbon atoms, alkoxy of 1 to 6 carbon atoms, or perfluoroalkoxy of 1 to 6 carbon atoms.

14. A compound of claim 13 wherein R, R', $R^1$, and $R^2$ are each hydrogen or alkyl of 1 to 6 carbon atoms.

15. A compound of claim 13 wherein $R^{3a}$ and $R^{3b}$ are each hydrogen or alkyl of 1 to 6 carbon atoms.

16. A compound of claim 13, wherein the remaining $R^4$ to $R^7$ are each independently, hydrogen, halogen, alkyl of 1 to 8 carbon atoms, or alkoxy of 1 to 6 carbon atoms.

17. A compound of claim 13, wherein $R^4$ and $R^5$ are, independently, hydrogen, halogen, alkyl of 1 to 8 carbon atoms, or alkoxy of 1 to 6 carbon atoms, and $R^6$ and $R^7$, together with the carbon atoms to which they are attached, form a monocyclic cycloalkyl of 3 to 8 carbon atoms.

18. A compound of claim 13, wherein $R^6$ and $R^7$, together with the carbon atoms to which they are attached, form a monocyclic cycloalkyl of 3 to 8 carbon atoms optionally substituted with one to five substituents each independently selected from alkyl, halogen, or alkoxy groups.

19. A compound of claim 18, wherein $R^4$ and $R^5$ are, independently, hydrogen, alkyl of 1 to 6 carbon atoms, alkoxy of 1 to 4 carbon atoms, or halogen.

20. A compound of claim 19 wherein $R^1$ and $R^2$ are each hydrogen or alkyl of 1 to 6 carbon atoms.

21. A compound of claim 13, wherein $R^6$ and $R^7$, together with the carbon atoms to which they are attached, form a monocyclic cycloalkyl of 3 to 8 carbon atoms optionally substituted with one to five substituents each independently selected from alkyl groups of 1 to 6 carbon atoms, halogens, or alkoxy groups of 1 to 6 carbon atoms.

22. A compound of claim 21, wherein $R^4$ and $R^5$ are, independently, hydrogen, alkyl of 1 to 6 carbon atoms, alkoxy of 1 to 4 carbon atoms, or halogen.

23. A compound of claim 22 wherein R, R', $R^1$, and $R^2$ are each hydrogen.

24. A compound of claim 1 which is:
(±)-1-(3,6,7,8-tetrahydro-2H-indeno[4,5-b]furan-2-yl)methanamine,
(+)-1-(3,6,7,8-tetrahydro-2H-indeno[4,5-b]furan-2-yl)methanamine,
(−)-1-(3,6,7,8-tetrahydro-2H-indeno[4,5-b]furan-2-yl)methanamine,
(±)-1-(2,3,6,7,8,9-hexahydronaphtho[1,2-b]furan-2-yl)methanamine,
(+)-1-(2,3,6,7,8,9-hexahydronaphtho[1,2-b]furan-2-yl)methanamine,
(−)-1-(2,3,6,7,8,9-hexahydronaphtho[1,2-b]furan-2-yl)methanamine,
(±)-1-(5-methyl-3,6,7,8-tetrahydro-2H-indeno[4,5-b]furan-2-yl)methanamine,
(+)-1-(5-methyl-3,6,7,8-tetrahydro-2H-indeno[4,5-b]furan-2-yl)methanamine,
(−)-1-(5-methyl-3,6,7,8-tetrahydro-2H-indeno[4,5-b]furan-2-yl)methanamine,
(±)-1-(2,3-dihydronaphtho[1,2-b]furan-2-yl)methanamine,
(+)-1-(2,3-dihydronaphtho[1,2-b]furan-2-yl)methanamine,
(−)-1-(2,3-dihydronaphtho[1,2-b]furan-2-yl)methanamine,
(±)-1-(2,3,5,6,7,8-hexahydronaphtho[2,3-b]furan-2-yl)methanamine,
(±)-1-(1,2,6,7,8,9-hexahydronaphtho[2,1-b]furan-2-yl)methanamine,
(2R*)-1-[(2R*)-3,6,7,8-tetrahydro-2H-indeno[4,5-b]furan-2-yl]ethylamine,
(±)-1-(4-chloro-3,6,7,8-tetrahydro-2H-indeno[4,5-b]furan-2-yl)methanamine,
(−)-1-(4-chloro-3,6,7,8-tetrahydro-2H-indeno[4,5-b]furan-2-yl)methanamine,
(+)-1-(4-chloro-3,6,7,8-tetrahydro-2H-indeno[4,5-b]furan-2-yl)methanamine,
(±)-1-(4-chloro-3,6,7,8-tetrahydro-2H-indeno[4,5-b]furan-2-yl)-N-methylmethanamine,
(±)-1-(5-chloro-3,6,7,8-tetrahydro-2H-indeno[4,5-b]furan-2-yl)methanamine,
(−)-1-(5-chloro-3,6,7,8-tetrahydro-2H-indeno[4,5-b]furan-2-yl)methanamine, or
(+)-1-(5-chloro-3,6,7,8-tetrahydro-2H-indeno[4,5-b]furan-2-yl)methanamine.

25. A composition comprising at least one compound of formula 1:

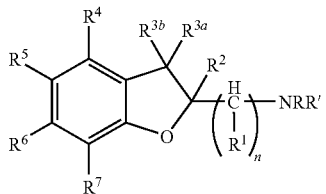

Formula 1 or pharmaceutically acceptable salts thereof;
wherein
- R and R' are, independently, hydrogen, alkyl of 1 to 6 carbon atoms;
- alternatively R and R' can be taken together with the nitrogen to which they are attached to form a ring containing 2-5 carbon atoms;
- $R^1$ and $R^2$ are each, independently, hydrogen, alkyl of 1 to 6 carbon atoms, cycloalkyl of 3 to 6 carbon atoms, or perfluoroalkyl of 1 to 6 carbon atoms;
- $R^{3a}$ and $R^{3b}$ are, independently, hydrogen, halogen, hydroxyl, alkyl of 1 to 6 carbon atoms, perfluoroalkyl of 1 to 6 carbon atoms, alkoxy of 1 to 6 carbon atoms, or perfluoroalkoxy of 1 to 6 carbon atoms;
- two adjacent substituents selected from $R^4$ and $R^5$, or $R^5$ and $R^6$, or $R^6$ and $R^7$, together with the carbon atoms to which they are attached, form a monocyclic cycloalkyl of 3 to 8 carbon atoms optionally substituted at a single carbon atom with a cycloalkyl of 3 to 5 carbon atoms;
- the remaining $R^4$ to $R^7$ substituents are, independently, hydrogen, halogen, cyano, hydroxyl, carboxyl, alkyl of 1 to 8 carbon atoms, perfluoroalkyl of 1 to 6 carbon atoms, alkoxy of 1 to 6 carbon atoms, perfluoroalkoxy of 1 to 6 carbon atoms, aryl of 5 to 10 carbon atoms, aryloxy of 5 to 10 carbon atoms, alkenyl of 2 to 8 carbon atoms, alkanoyl of 2 to 6 carbon atoms, alkanoyloxy of 2 to 6 carbon atoms, carboalkoxy of 2 to 6 carbon atoms, carboxamido, alkanamido of 2 to 6 carbon atoms, alkanesulfonamido of 1 to 6 carbon atoms, amino, monoalkylamino of 1 to 6 carbon atoms, dialkylamino of 1 to 6 carbon atoms per alkyl moiety, cycloalkyl of 3 to 8 carbon atoms; and
- n is 1, 2 or 3;
- wherein any cycloalkyl group is saturated or partially saturated, and any aryl, or cycloalkyl, group may optionally be substituted with 1 to 5 substituents independently selected from halogen, hydroxyl, alkyl of 1 to 6 carbon atoms, perfluoroalkyl of 1 to 6 carbon atoms, alkoxy of 1 to 6 carbon atoms, or perfluoroalkoxy of 1 to 6 carbon atoms;
- and one or more pharmaceutically acceptable carriers.

* * * * *